(12) United States Patent
Denis

(10) Patent No.: US 12,121,750 B1
(45) Date of Patent: Oct. 22, 2024

(54) SYSTEM AND METHOD OF REAL-TIME MOTION MANAGEMENT FOR BEAM RADIATION TREATMENT AND IMAGING

(71) Applicant: Carl Denis, Calgary (CA)

(72) Inventor: Carl Denis, Calgary (CA)

( * ) Notice: Subject to any disclaimer, the term of this patent is extended or adjusted under 35 U.S.C. 154(b) by 287 days.

(21) Appl. No.: 17/864,272

(22) Filed: Jul. 13, 2022

Related U.S. Application Data

(60) Provisional application No. 63/221,834, filed on Jul. 14, 2021.

(51) Int. Cl.
*A61B 90/00* (2016.01)
*A61N 5/10* (2006.01)

(52) U.S. Cl.
CPC .......... *A61N 5/1049* (2013.01); *A61N 5/103* (2013.01)

(58) Field of Classification Search
CPC ....... A61B 1/00147; A61B 1/04; A61B 1/042; A61B 34/00; A61B 1/045; A61B 34/10; A61B 34/20; A61B 2034/107; A61B 2034/2065; A61B 2090/364; A61B 5/721; A61B 5/72; A61B 2017/00053
See application file for complete search history.

(56) References Cited

U.S. PATENT DOCUMENTS 11,247,074 B2   2/2022   Wiersma
2021/0298868 A1*  9/2021   Rydberg ................ G16H 30/40

* cited by examiner

*Primary Examiner* — Don K Wong
(74) *Attorney, Agent, or Firm* — Banko IP Law PLLC; David A. Banko

(57) ABSTRACT

A system and method are disclosed for real-time motion management for beam radiation treatment and imaging, comprising a control system and a horizontal support structure, the horizontal support structure further comprising a fixed surface and a movable surface actuated by a robotic device, the control system further configured to receive target location information from one or more remote or local imaging devices or video output from a medical device providing treatment, generate a mapping of a patient location or a patient movement by scanning a visual field that includes the patient and the horizontal support structure, interpret the mapping to calculate a new position based on a detected deviation of a patient position or a patient movement from a target position, send instructions to the robotic device to actuate the movable surface to the new position; and receive position status information from the robotic device.

20 Claims, 28 Drawing Sheets

| TRANSLATION TYPE | TRANSLATION DIRECTION | ROTATION TYPE | ROTATION DIRECTION |
|---|---|---|---|
| X 2102 |  | ROLL 2108 | 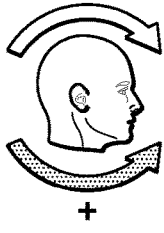 |
| Y 2104 | 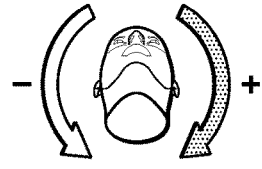 | PITCH 2110 |  |
| Z 2106 | 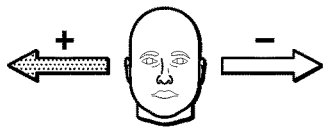 | YAW 2112 | 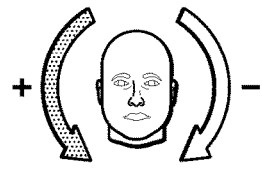 |
FIG. 21

2200

| Direction/Rotation | Move Amount | |
|---|---|---|
| Z (VRT) | 1.1 | mm |
| X (LNG) | -.2 | mm |
| Y (LAT) | 0 | mm |
| Yaw | 0 | deg |
| Roll | 1 | deg |
| Pitch | 1 | deg |

Movement Type:
Relative Move ▼

Submit

Clear

FIG. 22

SYSTEM AND METHOD OF REAL-TIME MOTION MANAGEMENT FOR BEAM RADIATION TREATMENT AND IMAGING

CROSS-REFERENCE TO RELATED APPLICATIONS

The present disclosure is related to that disclosed in the U.S. Provisional Application No. 63/221,834, filed Jul. 14, 2021, entitled "System and Method of Real-Time Motion Management for Beam Radiation Treatment and Imaging." U.S. Provisional Application No. 63/221,834 is assigned to the assignee of the present application. The subject matter disclosed in U.S. Provisional Application No. 63/221,834 is hereby incorporated by reference into the present disclosure as if fully set forth herein. The present invention hereby claims priority under 35 U.S.C. § 119(e) to U.S. Provisional Application No. 63/221,834.

TECHNICAL FIELD

The disclosure relates generally to movement correction during beam radiation therapy and radiological imaging, and more particularly to systems and methods of automatic correction of patient movement during therapy and imaging.

BACKGROUND

The trend in radiation therapy is moving toward higher doses of radiation over fewer treatments, advanced imaging techniques such as cone beam CT, FLASH Radiotherapy, increased beam angles, improved delivery techniques, etc. This trend, however, necessitates a corresponding increase in the accuracy of patient positioning. Currently available patient-positioning devices have proven inadequate, and their inability to accurately position patients has proven undesirable. These are often invasive, obstructive, claustrophobic, time consuming, and require specialized skills in patient immobilization to set up and maintain, which can lead to potential inefficiencies during patient treatment. This in turn can lead to delays during treatment and induce additional emotional stress in a patient during what can be an already difficult experience. Voluntary or involuntary movement of a patient during treatment or imaging may further lead to difficulties in treatment or imaging. These drawbacks are undesirable.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

FIG. 21 illustrates an example movement direction reference, according to an embodiment;

FIG. 22 illustrates the relative movement input, according to an embodiment;

DETAILED DESCRIPTION

Figure 1:
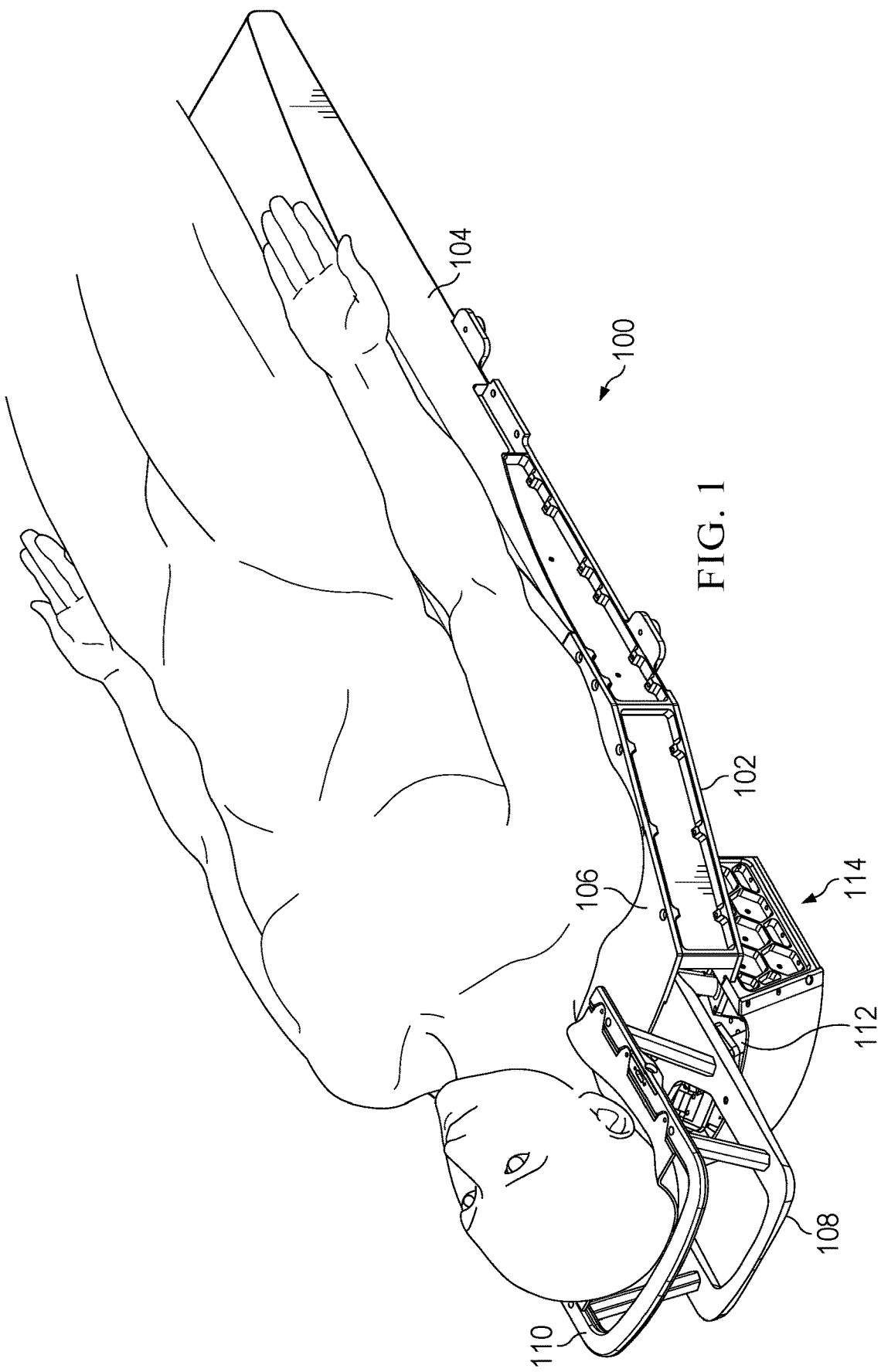
FIGS. 1-6 illustrate the movement correction couch overlay, according to an embodiment.

Aspects and applications of the invention presented herein are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

FIG. 1 illustrates a view of movement correction couch overlay 100, according to a first embodiment. According to an embodiment, real-time motion management system (RTMM system) 1000 (FIGS. 10A-B) comprises movement correction couch overlay 100 that uses robot-driven movement to automatically correct a patient's position during beam radiation therapy or treatment. According to embodiments, movement correction couch overlay 100 receives movement correction data either directly from (or by interpretation of) visual output media and without directly affecting primary system 1002 responsible for patient motion monitoring. RTMM system 1000 further comprises a flexible and modular design which provides for upgraded and expanded tools, as described in further detail herein. In the illustrated embodiment of FIG. 1, movement correction couch overlay 100 comprises primary base 102, support cushion 104, friction modifier plate 106, base headboard 108, headrest attachment 110, hexapod robot 112, and robot enclosure 114.

Figure 2:
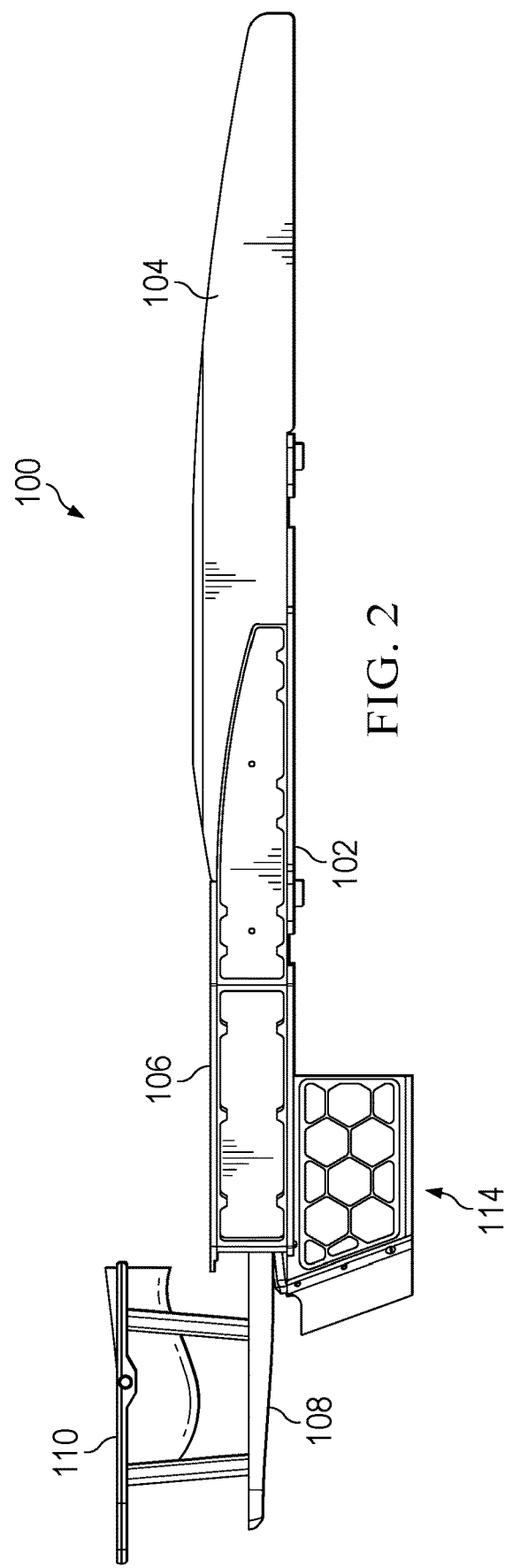
Figure 4:
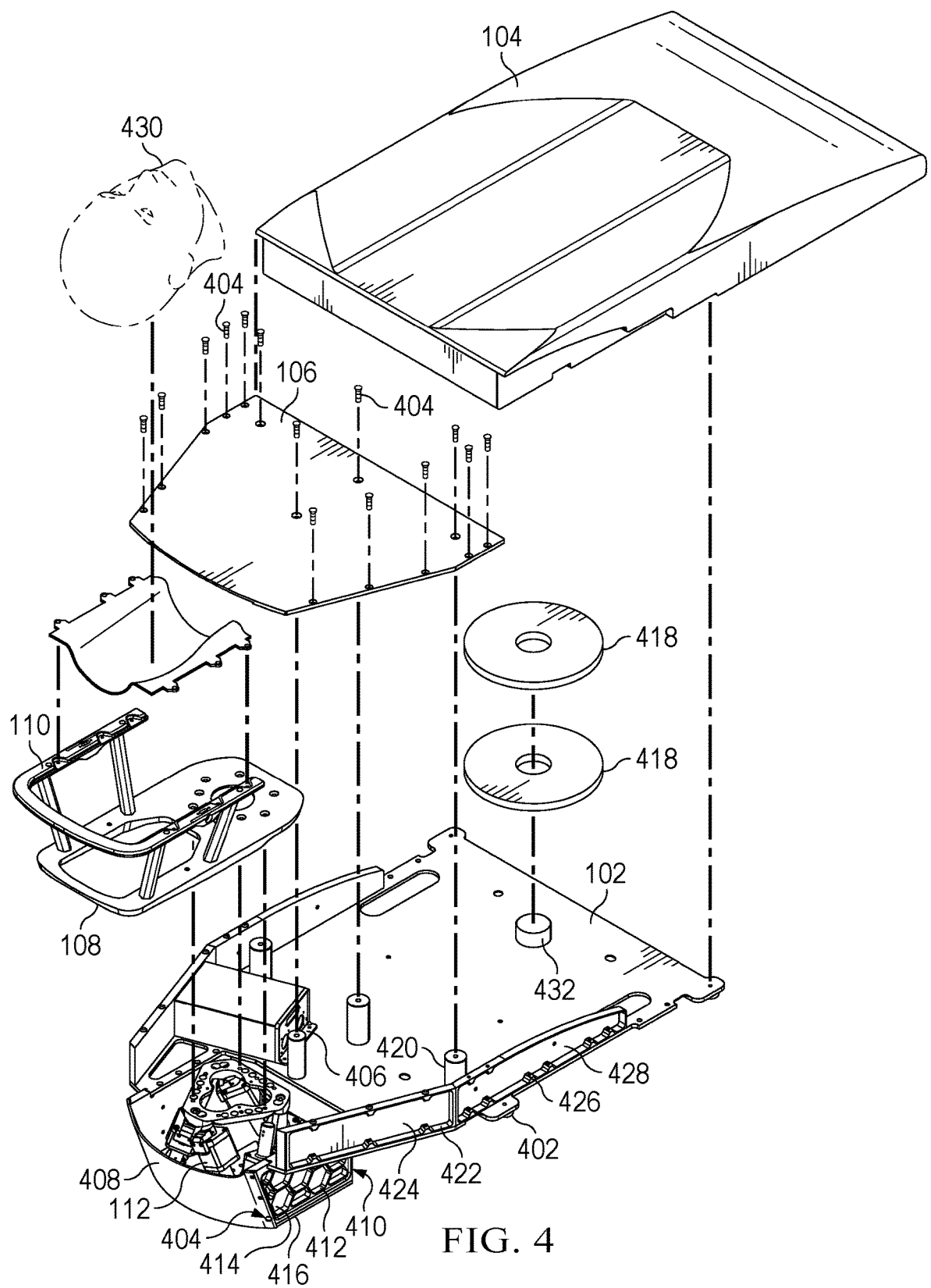

FIG. 2 illustrates a side view of movement correction couch overlay 100, according to the first embodiment. Primary base 102 comprises a bottom member whose lower surface couples to the upper surface of a treatment bench (or couch) and whose top member comprises a friction modifier plate that provides a support surface for the patient's upper torso through to mid-neck. This anatomical region may need to move when adjusting the position of the patient's head, and this movement is facilitated by a hard, low-friction plate, which can be replaced with a plate constructed with a softer material and/or higher friction coefficient, when such movement is not desired or when required for patient comfort, according to particular needs. According to an embodiment, primary base 102 comprises several joined components, which may include, for example, a bottom adaptor plate, a top adaptor plate, adapter support walls, adapter support wall foam, and flex-reducing wall foam, as described in further detail below. Patient support cushion 104 couples to primary base 102 and provides a support surface for the patient. An upper surface of patient support cushion 104 may form a substantially continuous patient support surface with the upper surface of primary base 102, such as, for example, friction modifier plate 106, to support the torso of a patient. The head of a patient may be supported by base headboard 108. Headrest attachment 110 couples to the upper surface of base headboard 108 and provides a mating surface for phantom head 430 (FIG. 4). As described in further detail below, various other headrest devices may be coupled to base headboard 108 to provide support for the head of a patient, while the torso of the patient is supported by primary base 102. Base headboard 108 couples to hexapod robot 112 which provides movement of base headboard 108 independently of the stationary patient support surfaces of primary base 102 (e.g., patient support cushion 104 and friction modifier plate 106). In this embodiment, robot 112 is mounted within robot enclosure 114, which is coupled to the bottom side of primary base 102.

Figure 3:
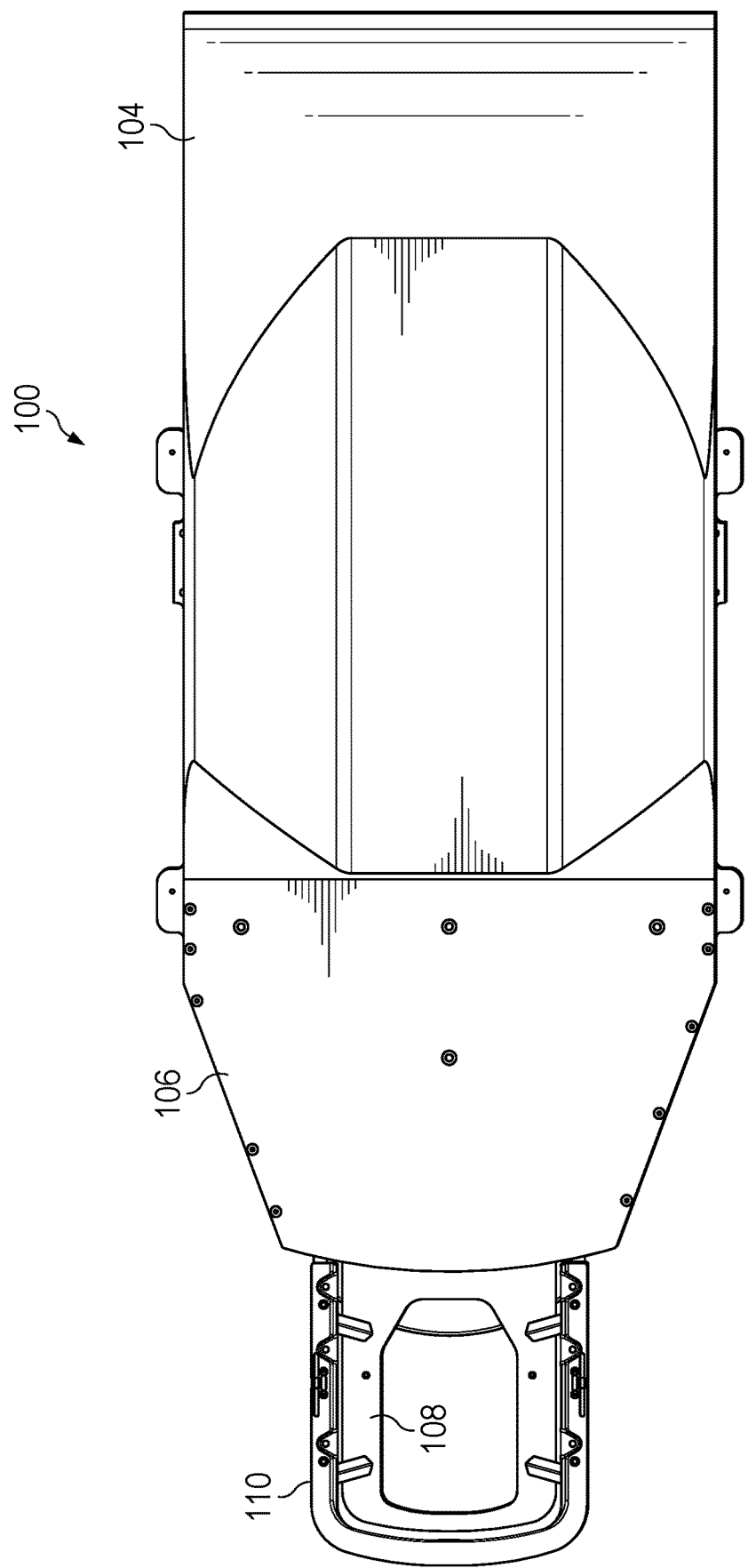

FIG. 3 illustrates a top view of movement correction couch overlay 100, according to the first embodiment. As described in further detail below, RTMM system 1000 controls robot 112 to automatically move base headboard 108 to correct for movement of a patient during treatment or imaging. By way of example only and not by way of limitation, embodiments of RTMM system 1000 provide automatic correction for patient head movement during radiological imaging and treatment by detecting (or predicting) a patient head movement and adjusting base headboard 108 independently of the patient's body to compensate for the movement. In one embodiment, headrest attachment 110 comprises four raised supports that couple to base headboard 108. According to some embodiments, headrest attachment 110 is movable with respect to base headboard 108 to provide various options for placement of a patient's head. According to some embodiments, headrest attachment 110 comprises pins on either side of the module that are received by holes in the surface of base headboard 108. The pins may be inserted into various holes to allow different positions of headrest attachment 110 with respect to base headboard 108. According to embodiments, an open face thermoplastic mask may be attached to base headboard 108 using interface points located around the perimeter of base headboard 108. Various embodiments and configurations of base headboard 108 and headrest attachment 110 may be coupled with the various embodiments of movement correction couch overlay 100 described herein, according to particular needs.

According to some embodiments, primary base 102 of movement correction couch overlay 100 comprises a substantially flat and couch-indexable base to which couples other components of movement correction couch overlay 100, as shown in the following FIGURES.

FIG. 4 illustrates an exploded isometric view of movement correction couch overlay 100, according to the first embodiment. Referring to the embodiment illustrated in FIGS. 4-6, movement correction couch overlay 100 comprises index bars 402, fasteners 404, control box 602 (FIG. 6), robot 112, control box adapter frame 406, base headboard 108, headrest attachment 110, front robot cover 108, rear robot cover 410, left hex wall of robot enclosure 604, left hex wall of robot enclosure foam 606, right hex wall of robot enclosure 412, right hex wall of robot enclosure foam 414, robot enclosure base plate 416, friction modifier plate 106, primary base 102, patient support cushion 104, counterweights 418, supports 420, primary base wall 422, primary base wall foam 424, bed wall with control slot 608, bed wall with control slot foam 610, left flex-reducing wall 612, left flex-reducing wall foam 614, right flex-reducing wall 426, right flex-reducing wall foam 428, phantom head model 430, and counterweight coupling member 432. Although movement correction couch overlay 100 is illustrated as comprising index bars 402, fasteners 404, control box 602, robot 112, control box adapter frame 406, base headboard 108, headrest attachment 110, front robot cover 108, rear robot cover 410, left hex wall of robot enclosure 604, left hex wall of robot enclosure foam 606, right hex wall of robot enclosure 412, right hex wall of robot enclosure foam 414, robot enclosure base plate 416, friction modifier plate 106, primary base 102, support cushion 104, counterweight 418, supports 420, primary base wall 422, primary base wall foam 424, bed wall with control slot 608, bed wall with control slot foam 610, left flex-reducing wall 614, left flex-reducing wall foam 614, right flex-reducing wall 426, right flex-reducing wall foam 428, phantom head model 430, and counterweight coupling member 432, embodiments contemplate any suitable quantity or combination of these, according to particular needs.

Robot 112 receives power and communication from control box 602, which houses electronic power and communication components for robot 112. Control box 602 is coupled to primary base 102 by control box adapter frame 406. As disclosed above, robot 112 is mounted within enclosure 114. Enclosure 114 comprises front robot cover 408, rear robot cover 410, left hex wall of robot enclosure 604, left hex wall of robot enclosure foam 606, right hex wall of robot enclosure 412, right hex wall of robot enclosure foam 414 and robot enclosure base plate 416. According to embodiments, robot 112 is coupled by fasteners 404 to robot enclosure base plate 416.

Friction modifier plate 106 couples to primary base 102 by one or more fasteners 404. According to an embodiment, primary base 102 comprises one or more supports 420 which provide additional support to friction modifier plate 106. Friction modifier plate 106 is supported on its outer left and right edges by one or more walls coupled to primary base 102. According to an embodiment, primary base 102 comprises primary base wall 422, bed wall with control slot 608, and two walls which reduce flexing of primary base 102 (left flex-reducing wall 612 and right flex-reducing wall 426). Left flex-reducing wall 612 may comprise communication cable ties, which are used to route cables from control box 602.

Figure 5:
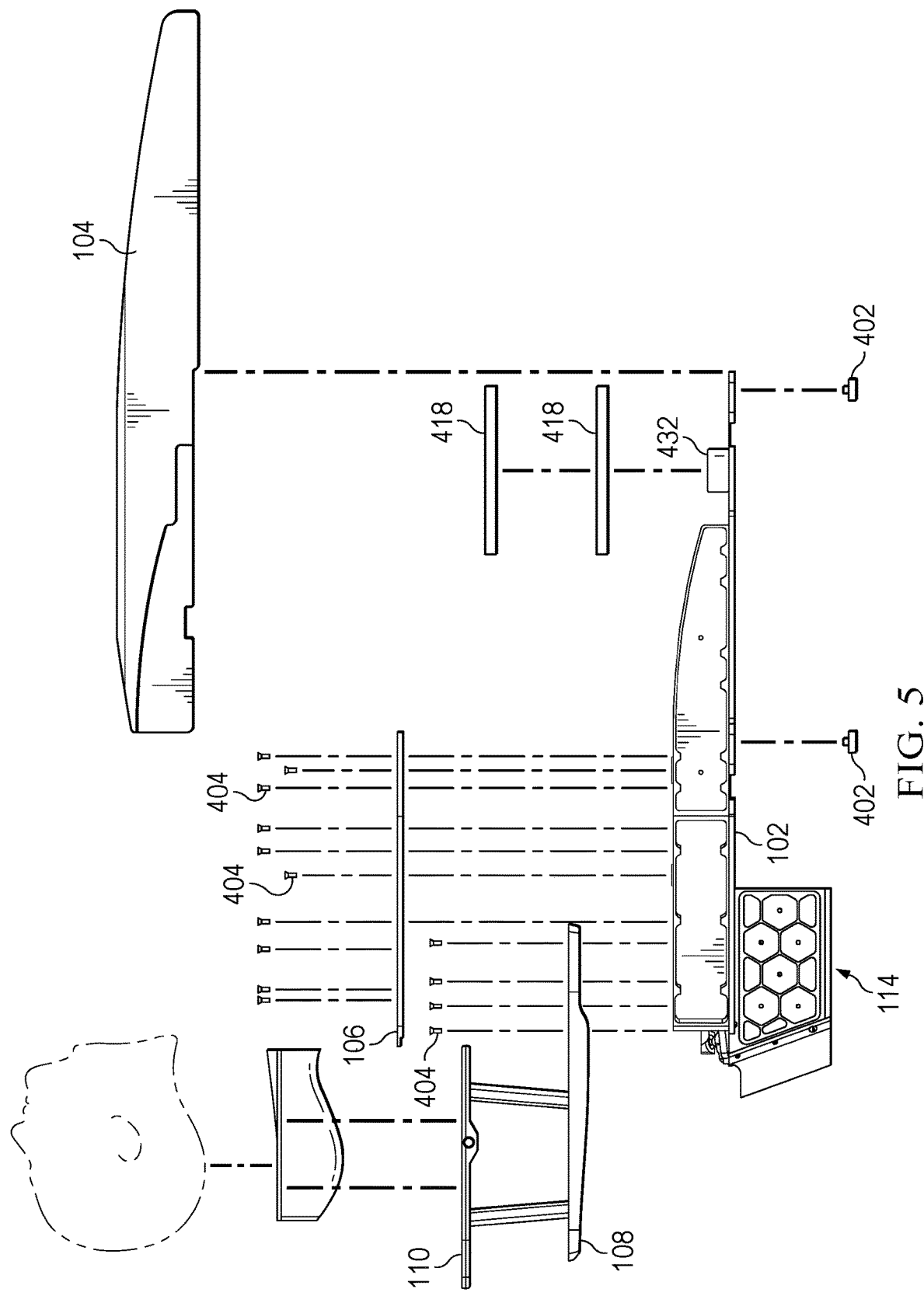

FIG. 5 illustrates an exploded side view of movement correction couch overlay 100, according to the first embodiment. In this view of movement correction couch overlay 100, coupling of patient support cushion 104, friction modifier plate 106, and fasteners 404 to primary base 102 is shown. Counterweights 418 slidably mount over a coupling member 432 (such as, for example, a peg or dowel) coupled to the upper surface of primary base 102. According to embodiments, one or more counterweights 418 are sized, located, configured, and weighted to balance robot 112, robot enclosure 114, and head baseboard 108, which may extend a significant distance over the edge of the treatment surface. In the illustrated embodiment, counterweights 418 are located beneath patient support cushion 104, which is coupled to primary base 102 over the counterweights 418 by aligning grooves of torso cushion 104 with left flex-reducing wall 612 and right flex-reducing wall 426 of primary base 102.

Figure 6:
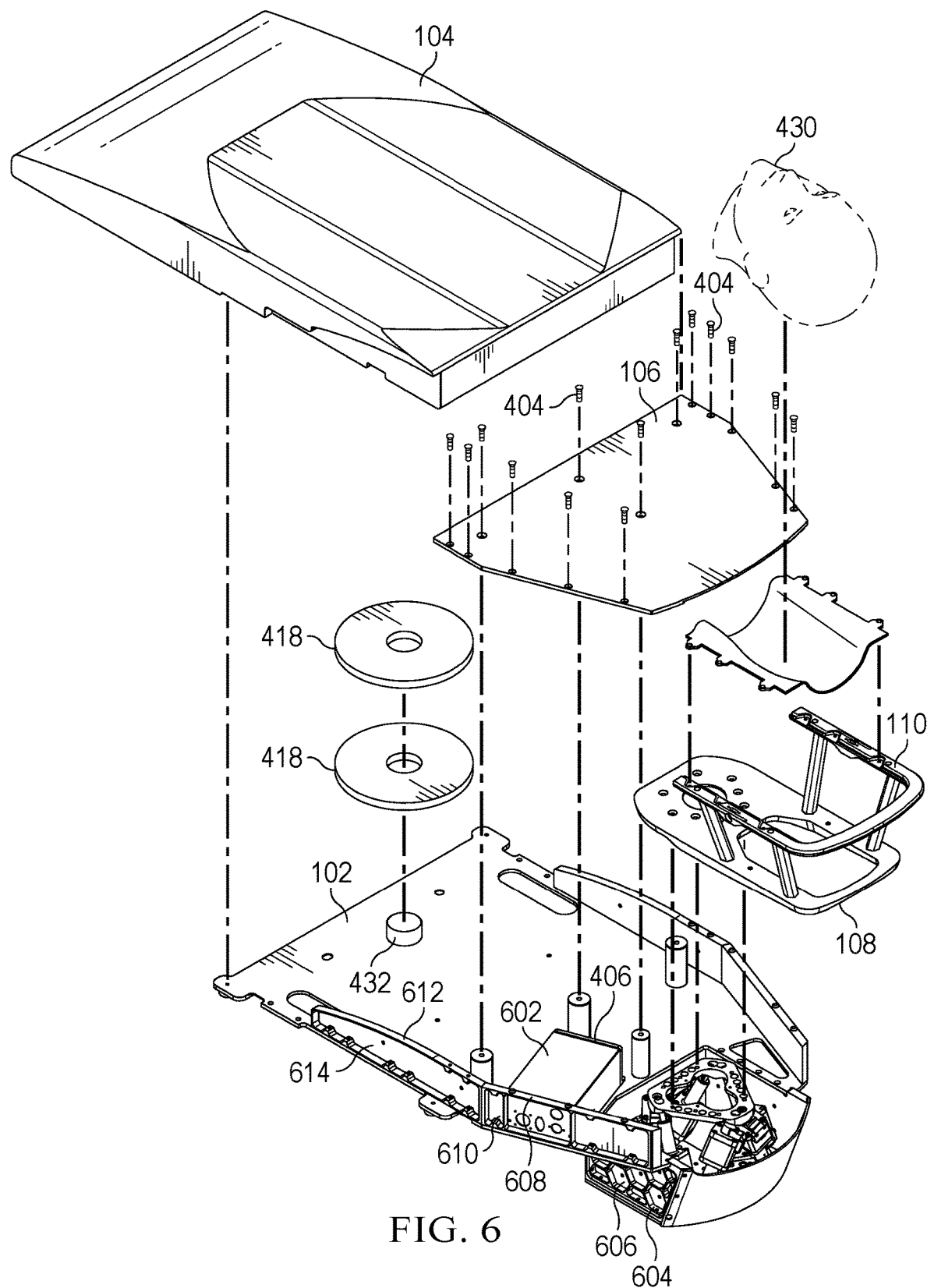

FIG. 6 illustrates a second exploded isometric view of movement correction couch overlay 100, according to the first embodiment. In one embodiment, movement correction couch overlay 100 couples to the upper surface of a treatment bed, couch, or other treatment surface (hereinafter "treatment couch") by one or more removable and interchangeable index bars 402 comprising pins that couple to one or more receptacles on the underside of primary base 102. Primary base 102 may couple by index bars 402 to a treatment couch wherein index bar tabs couple to similarly shaped slots in the surface of the treatment couch so that movement correction couch overlay 100 is securely and removably coupled to the treatment couch and may be repeatedly placed in the same position after movement correction couch overlay 100 is removed. Although movement correction couch overlay 100 is illustrated with particular index bars 402, embodiments contemplate any suitable index bars 402 such as proprietary index bars utilized by various treatment couches, according to particular needs. Embodiments contemplate any suitable coupling mechanism to reproducibly position movement correction couch overlay 100 in substantially the same placement on a treatment couch.

As described in further detail below, phantom head model 430 couples with headrest attachment 110 and comprises high-density spheres that serve as an analogue to tumor locations in a patient's head and is utilized as a uniform test case for calibrating and testing equipment in a treatment setting.

Figure 7:
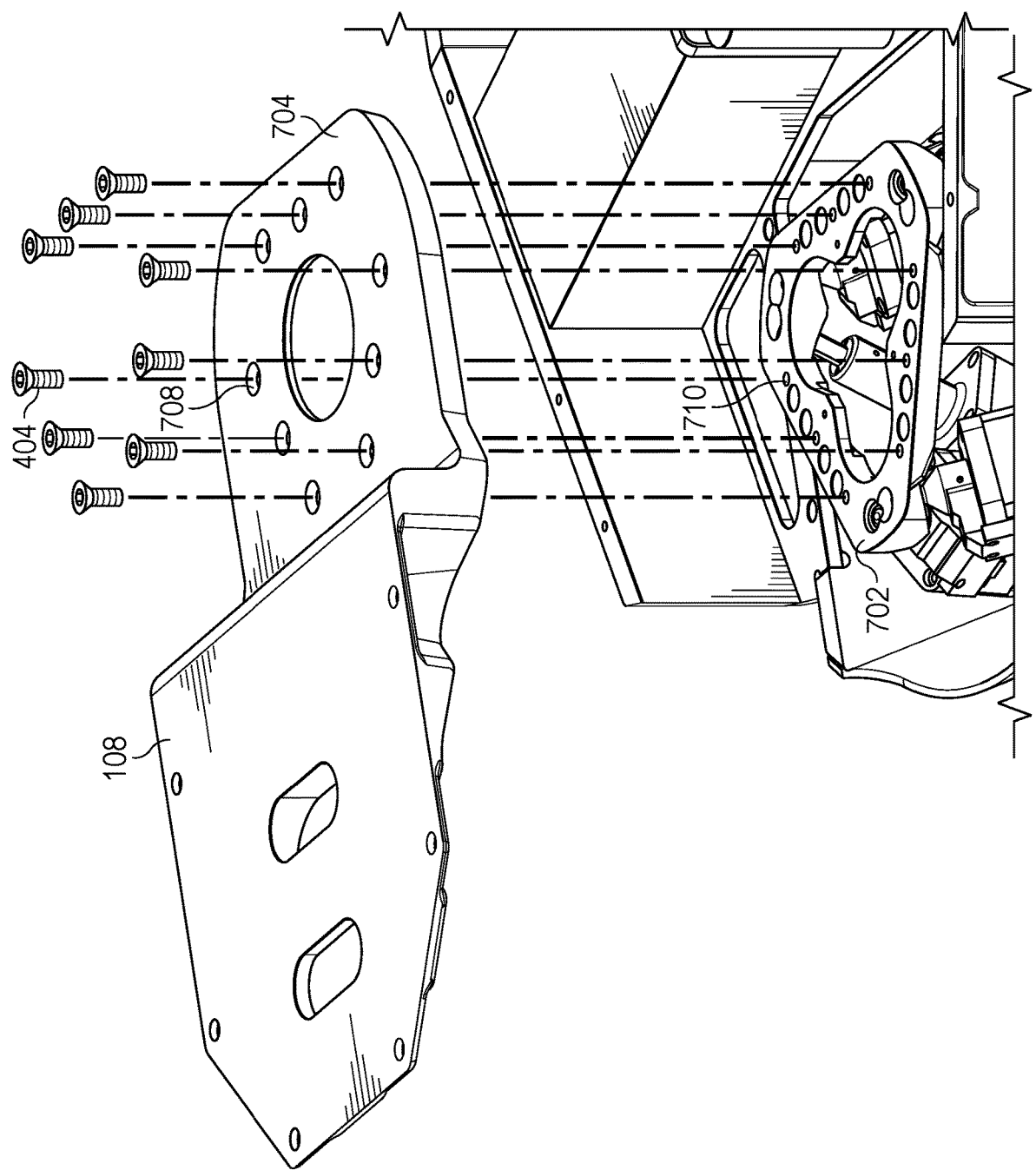
FIGS. 7-8 illustrate the hexapod robot of the movement correction couch overlay, according to an embodiment.
Figure 8:
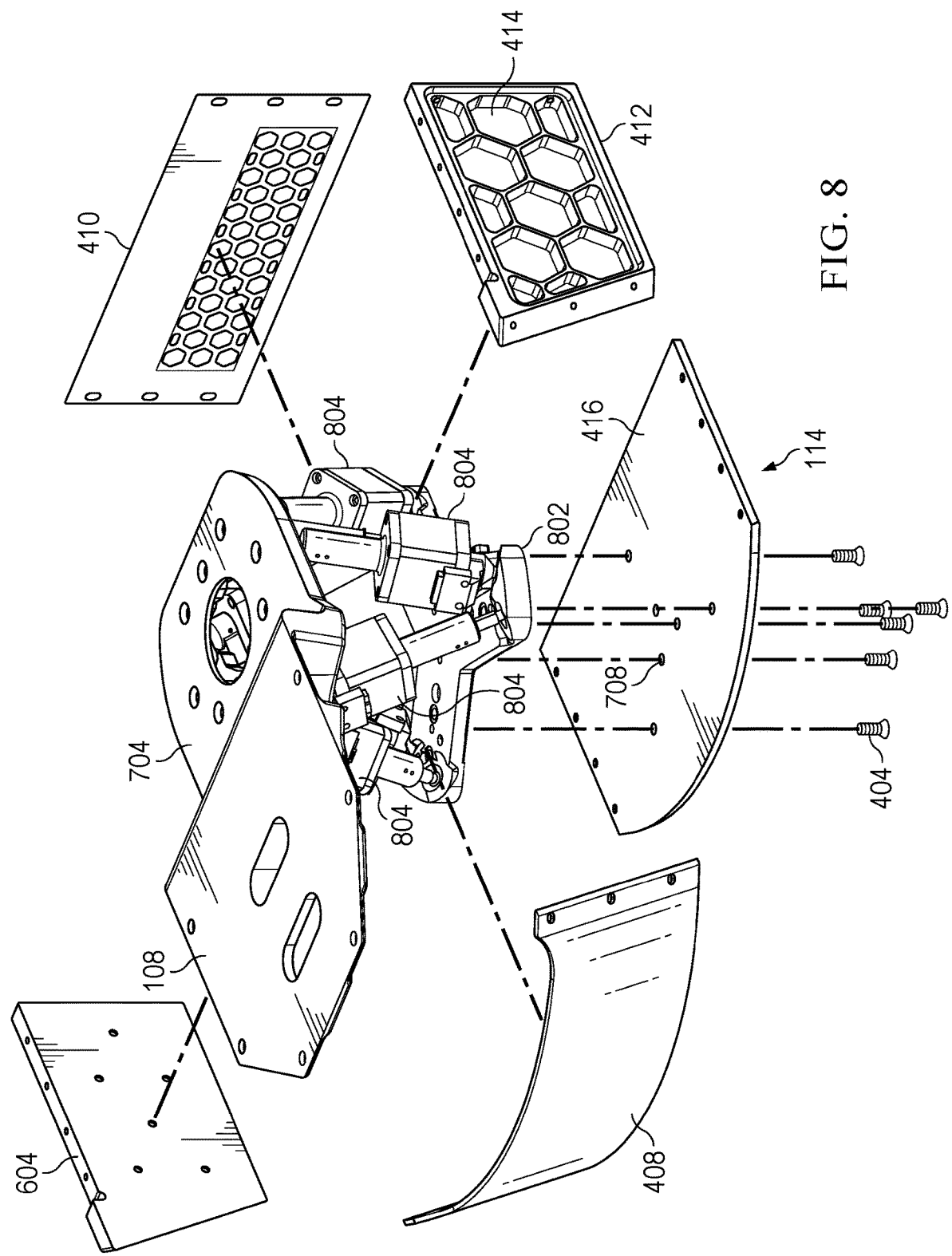

FIGS. 7 and 8 illustrate hexapod robot 112 of movement correction couch overlay 100, according to an embodiment. Robot 112 moves a movement correction surface (such as, for example, base headboard 108) in six degrees of freedom with respect to the patient support platform. As described in further detail below, RTMM system 1000 identifies a deviation in a patient's position relative to a required target location and reduces this deviation through corrective movement via robot 112. Robot 112 of movement correction couch overlay 100 is controlled by RTMM system 1000, which uses an internal coordinate system to allow the user to customize the center of rotation and translation to line up with a target point within the patient's cranial area. As described in further detail below, movement of robot 112 can be manually set by the user or automatically managed by RTMM system 1000 through the processing and interpretation of external data to determine required movements for positional correction to automatically correct patient positioning during treatment or imaging.

As disclosed above, robot enclosure 114 comprises front robot cover 408, rear robot cover 410, left hex wall of robot enclosure 604, left hex wall of robot enclosure foam 606, right hex wall of robot enclosure 412, right hex wall of robot enclosure foam 414 and robot enclosure base plate 416, and one or more fasteners 404. In one embodiment, robot 112 is mounted to robot enclosure base plate 416 by one or more fasteners 404 through receiving apertures 708, and robot enclosure base plate 416 is secured by one or more fasteners 404 to front robot cover 408, rear robot cover 410, left wall 604, and right wall 412 of robot enclosure 114. Robot enclosure 114 containing the mounted robotic device is coupled by a plurality of fasteners 404 to primary base 102 of movement correction couch overlay 100 in a position beneath the patient position correction surface, which, in the illustrated embodiment, is the head of the patient. Robot 112 comprises mount 702. Mount 702 comprises apertures 710 which provide mating surfaces for fasteners 404 passing through apertures 708 to couple bracket 704 of base headboard 108 to mount 702.

In some embodiments, mechanical actuators 804 are situated within robot enclosure 114 and control the position of a movement correction surface coupled to mount 702 through retraction and advancement of one or more of various actuators 804. In addition, or as an alternative, pneumatic or hydraulic actuators may be used for adjustment of a movement correction surface, such as, for example, base headboard 108. One limitation of a hexapod robot with mechanical actuators is that, due to the physical properties of its components, it cannot be placed directly under the patient's head, resulting in an isocenter located away from an optimal position, reducing the range of movement. Pneumatic, hydraulic, or other like air- or fluid-controlled movement control components may be constructed from non-metallic materials (such as, for example, plastic, composites, rubbers, and other like materials, disclosed herein), which provide for placement of movement control components nearer to a treatment area of a patient. By using air- or fluid-pressure, sensors, tubing, pipes, valves, reservoirs, and the like, RTMM system 1000 may be configured to provide more options of placement and potentially reduce noise and vibration compared to screw and motor-based actuators of hexapod robot 112.

In addition, it will be readily apparent to one having skill in the art that, although aspects of the illustrated embodiment are described in connection with head movement of a human patient during radiological treatment and imaging, embodiments are not so limited. The methodology applied to the manipulation of a patient's head position in the given embodiment may in turn be applied to the positional adjustment of other body parts. Embodiments contemplate modifying the patient support surface and correction support surface to provide positioning of a patient's torso, limbs, and the like. These platforms may differ in coupling for the targeted body part and placement on the treatment couch but operate according to the principles outlined herein, as would be apparent to one having skill in the art from the present disclosure.

In addition to moving a single anatomical region or body part (such as, for example, the head independent of the body), additional or alternative actuators or controllable motion devices (such as, for example, airbag, pneumatic or hydraulic fixtures, and the like, as disclosed herein) may be coupled to primary base 102 and utilized to move secondary anatomical areas such as C-Spine (neck) independently from the head, pelvis independently from the torso, or other anatomical regions or parts independently from different other anatomical regions or parts. In addition, or as an alternative, more than one anatomical area may be moved with consideration of range of motion and patient comfort independent or in concert with another adjoined anatomical part or region.

Material selection for construction of movement correction couch overlay 100 is determined through need and the operation area of the various components of movement correction couch overlay 100. Operation areas are divided into treatment and non-treatment areas, with treatment areas, such as, for example, base headboard 108, requiring radio-translucent materials to minimize interaction with a radiation beam path. By way of example only and not by way of limitation, treatment areas, such as, for example, base headboard 108, are constructed from one or more of a carbon-fiber reinforced polymer, or any other suitable polymer, including but not limited to any suitable fiber-reinforced polymer, such as KEVLAR, fiber glass, hemp, or the like, including the foregoing sandwiched over a low-density core of air, foam, or other suitable material.

Material selection for non-treatment areas may be determined by mechanical requirements. By way of example only and not by way of limitation, primary base 102 (and any of its constituent or joined components) may comprise a material that is rigid and provides little or no deflection or flex under load. In one embodiment, primary base 102 (and any of its constituent or joined components) may be constructed from one or more of: ferrous and non-ferrous metals (i.e. aluminum, titanium, steel, their alloys, and the like), composites (i.e. carbon-fiber, fiberglass), thermoplastic, and/or thermosetting plastic, and the like. By way of further example only and not by way of limitation, friction modifier plate 106 may be formed from a rigid material having a low friction coefficient. In addition, or as an alternative, friction modifier plate 106 may comprise alternate or optional materials, as disclosed herein. According to embodiments, friction modifier plate 106 is constructed from one or more of ferrous and non-ferrous metals (i.e. aluminum, titanium, steel, their alloys, and the like), composites (i.e. carbon-fiber, fiberglass), thermoplastic, and/or thermosetting plastic, and the like.

By way of an additional example only and not by way of limitation, patient support cushion 104 comprises a material that is soft for comfort, stable, and exhibits a friction coefficient suitable to keep a patient in position. In one embodiment, the torso cushion is constructed from, for example, polyurethane, EVA, plastic, and the like.

Although particular components are described as comprising particular materials or combinations of materials based on treatment or non-treatment operation area, embodiments contemplate selecting any suitable material for any particular component, according to particular needs.

Figure 9:
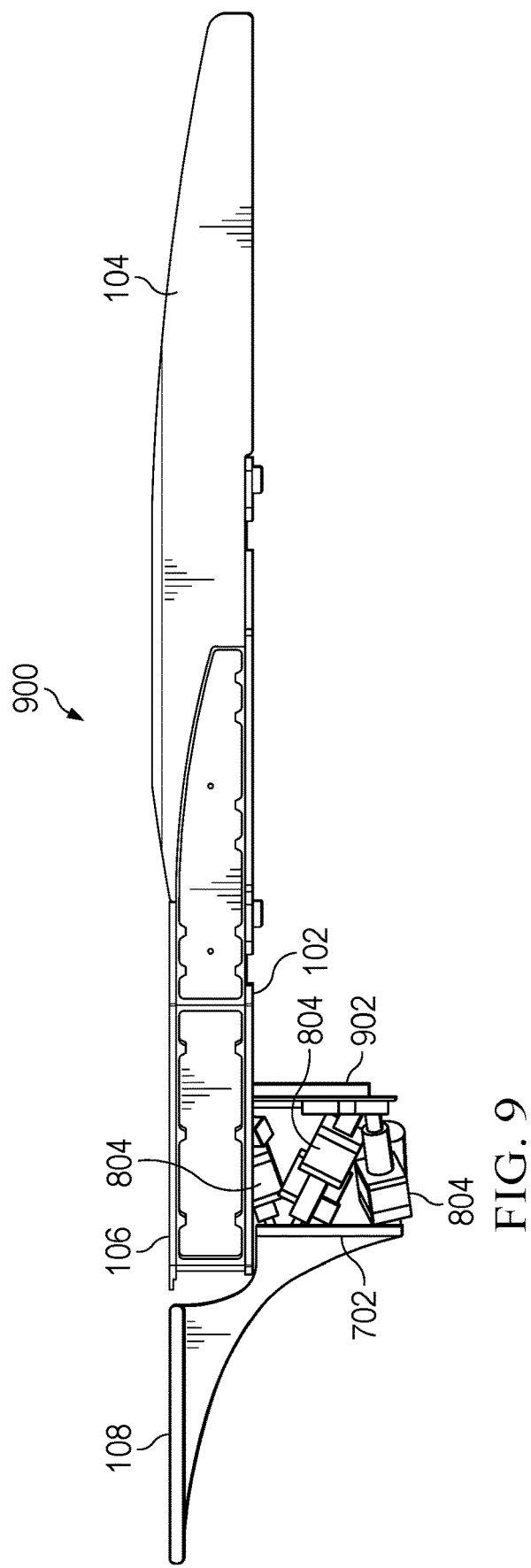
FIG. 9 illustrates the side-mounted robotic device, according to an embodiment.

FIG. 9 illustrates side-mounted robotic device 900, according to an embodiment. Although robot 112 of movement couch correction overlay 100 is shown and described as a movement control having a vertical orientation, embodiments contemplate mounting robot support 902 and mount 702 for robot 112 parallel to the treatment couch. According to embodiments, side-mounted robotic device 900 may be utilized to modify the range of motion of base headboard 108. Embodiments contemplate providing additional actuators 804 and/or support structures to reduce the strain on mechanical components of movement correction couch overlay 100 to compensate for this change in platform orientation relative to the force generated by the patient's head resting on head baseboard 108.

Figure 10A:
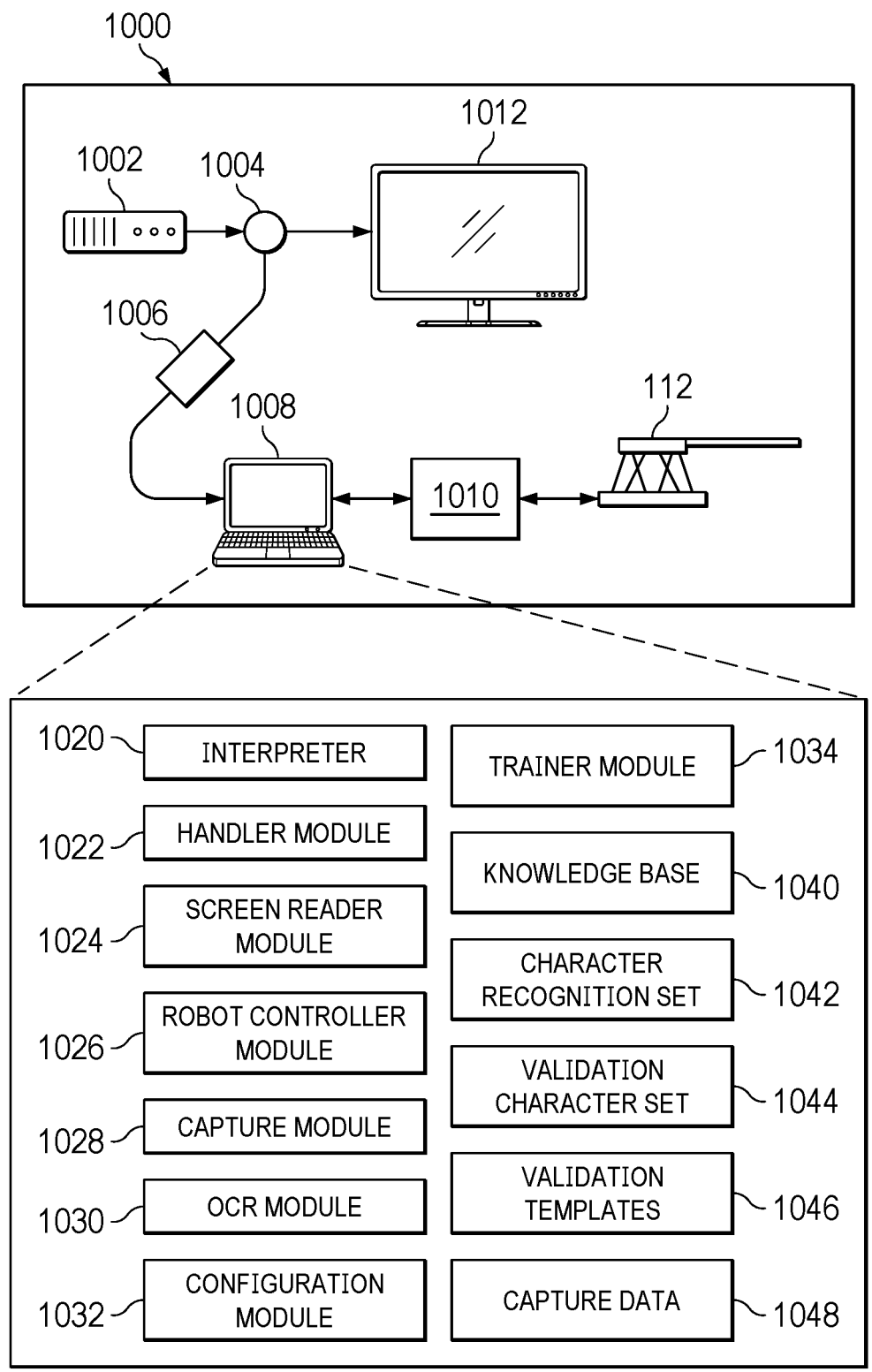
FIGS. 10A-10B illustrate the RTMM system, according to embodiments.

FIG. 10A illustrates RTMM system 1000, according to an embodiment.

RTMM system 1000 comprises a primary system 1002 (which may, according to embodiments, comprise the source of the primary system visual output received by signal splitter/duplicator 1004 and/or capture device 1006, as disclosed in greater detail below), computer 1008, controller 1010, and robot 112 of movement correction couch overlay 100. According to an embodiment, primary system 1002 is a patient monitoring system that displays patient movement data on primary system 1002 display device 1012. Although RTMM system 1000 is shown and described as comprising a single primary system 1002, a single primary system display device 1012, a single signal splitter/duplicator 1004, a single capture device 1006, a single computer 1008, a single controller 1010, and a single robot 112, embodiments of RTMM system 1000 may comprise any number or combination of primary systems, primary system display devices, signal splitter/duplicators, capture devices, computers, controllers, and robots, according to particular needs. RTMM system 1000 comprising primary system 1002, signal splitter/duplicator 1004, capture device 1006, computer 1008, controller 1010, and robot 112 may operate on one or more computers that are integral to or separate from the hardware and/or software that support primary system 1002, primary system display device 1012, signal splitter/duplicator 1004, capture device 1006, computer 1008, controller 1010, and robot 112. Primary system 1002 and computer 1008 may include any suitable input device, such as a keypad, mouse, touch screen, microphone, or other device to input information. An output device may convey information associated with the operation of primary system 1002, signal splitter/duplicator 1004, capture device 1006, computer 1008, controller 1010, and robot 112 including digital or analog data, visual information, or audio information. Primary system 1002 and computer 1008 may include fixed or removable computer-readable storage media, including a non-transitory computer readable medium, magnetic computer disks, flash drives, CD-ROM, in-memory device or other suitable media to receive output from and provide input to RTMM system 1000. Primary system 1002 and computer 1008 may include one or more processors and associated memory to execute instructions and manipulate information according to the operation of RTMM system 1000 described herein. In addition, or as an alternative, embodiments contemplate executing the instructions on primary system 1002 and computer 1008 that cause one or more computers to perform functions of the method. An apparatus implementing special purpose logic circuitry, for example, one or more field programmable gate arrays (FPGA) or application-specific integrated circuits (ASIC), may perform functions of the methods described herein. Further examples may also include articles of manufacture including tangible non-transitory computer-readable media that have computer-readable instructions encoded thereon, and the instructions may comprise instructions to perform functions of the methods described herein. By way of example only and not of limitation, further embodiments include any number of one or more processing units, including, for example, one or more graphical processing units (GPUs), programmed to create, manipulate, render for display, analyze, recognize, identify, perform machine learning and/or artificial intelligence processes for image recognition, object detection, or tagging, or otherwise process one or more graphs, images, alphanumeric text, graphics, or other data, according to particular needs.

RTMM system 1000 may operate on one or more separate computers, a network of one or more separate or collective computers, or may operate on one or more shared computers. In addition, RTMM system 1000 may comprise a cloud-based computing system having processing and storage devices at one or more locations, local to, or remote from primary system 1002, signal splitter/duplicator 1004, capture device 1006, computer 1008, controller 1010, and robot 112. In addition, each of one or more computers may be a workstation, personal computer (PC), network computer, notebook computer, tablet, personal digital assistant (PDA), cell phone, telephone, smartphone, mobile device, wireless data port, augmented or virtual reality headset, or any other suitable computing device. In an embodiment, one or more users may be associated with RTMM system 1000. These one or more users may include, for example, a "treatment provider" or a "technician", handling treatment decisions, system setup, manual movement of RTMM system 1000, and the like. In addition, or as an alternative, these one or more users of RTMM system 1000 may include, for example, one or more computers programmed to autonomously handle, among other things, patient movement correction, setup, calibration, and/or one or more related tasks of the systems and methods, as described in further detail herein.

In one embodiment, each of primary system 1002, signal splitter/duplicator 1004, capture device 1006, computer 1008, controller 1010, and robot 112 be coupled with the network using a communications link, which may be any wireline, wireless, or other link suitable to support data communications between primary system 1002, signal splitter/duplicator 1004, capture device 1006, computer 1008, controller 1010, and robot 112 and a network during operation of RTMM system 1000. Although communication links are shown and described as generally coupling primary system 1002, signal splitter/duplicator 1004, capture device 1006, computer 1008, controller 1010, and robot 112 to each other or a wireless or wireline communication network, any of primary system 1002, signal splitter/duplicator 1004, capture device 1006, computer 1008, controller 1010, and robot 112 may communicate directly with each other or over a network, according to particular needs. In another embodiment, the network includes the Internet and any appropriate local area networks (LANs), metropolitan area networks (MANs), or wide area networks (WANs) coupling primary system 1002, signal splitter/duplicator 1004, capture device 1006, computer 1008, controller 1010, and robot 112 and one or more computers. For example, data may be maintained locally, or externally of, primary system 1002, signal splitter/duplicator 1004, capture device 1006, computer 1008, controller 1010, and robot 112 and made available to one or more associated users of primary system 1002, signal splitter/duplicator 1004, capture device 1006, computer 1008, controller 1010, and robot 112 using the network or in any other appropriate manner. Those skilled in the art will recognize that the complete structure and operation of the network and other components within RTMM system 1000 are not depicted or described. Embodiments may be employed in conjunction with known communications networks and other components.

In one embodiment, computer 1008 comprises control software for RTMM system 1000 providing for, among other things, control, calibration, and setup of robot 112. Computer 1008 comprises interpreter 1020, handler module 1022, screen reader module 1024, robot controller module 1026, capture module 1028, OCR module 1030, configuration module 1032, trainer module 1034, knowledge base 1040, character recognition set 1042, validation character set 1044, validation templates 1046, and capture data 1048. Although computer 1008 is described as comprising interpreter 1020, handler module 1022, screen reader module 1024, robot controller module 1026, capture module 1028, OCR module 1030, configuration module 1032, trainer module 1034, knowledge base 1040, character recognition set 1042, validation character set 1044, validation templates 1046, and capture data 1048, embodiments contemplate any suitable number of one or more of the foregoing at one or more locations local to, or remote from, RTMM system 1000. In addition, although modules are described as separate and distinct modules, embodiments contemplate one or more modules performed by the same software or hardware component, according to particular needs. For example, handler module 1022 and robot controller module 1026 may be the same device or a series of networked components. Transmission of data between the modules of the system can include methods such as direct data pipelines on the same computing system (such as running capture module 1028 as a subprocess of the main RTMM process), wired connections between separate machines, and wireless transmission of data between separate machines using transmitters and receivers RTMM system 1000 may perform a self-calibration during initialization, wherein hexapod robot 112 adjusts its movement before returning to a neutral position. As disclosed above, robot 112 of RTMM system 1000 receives power and control signals from controller 1010. Controller 1010 comprises a power switch and connections for one or more power cables and communication links. In one embodiment, controller 1010 comprising a control box receives electrical power through a power cable connector from a power cable connected to a standard wall outlet and receives control signals through a USB port receiving a USB cable connected with computer 1008. In one embodiment, robot 112 is controlled and powered by a main control box, which, receives robotic device instructions for movement or directions by computer 1008 or other device through either a wired or wireless connection. Although controller 1010 is described as comprising a single power connector and a single USB port, embodiments contemplate any suitable power source and any suitable data link, according to particular needs. Although disclosed as wired connections, embodiments contemplate any suitable data or power interface, as disclosed herein. For example, data interface may comprise wireless (WIFI, BLUETOOTH, or other like suitable wireless protocol). In addition, or in the alternative, power source may comprise a battery-powered source located, internal to, or external of, movement correction couch overlay 100, such as, for example, in a cavity formed within support cushion 104 and/or within the volume between friction modifier plate 106 and primary base 102.

Figure 10B:
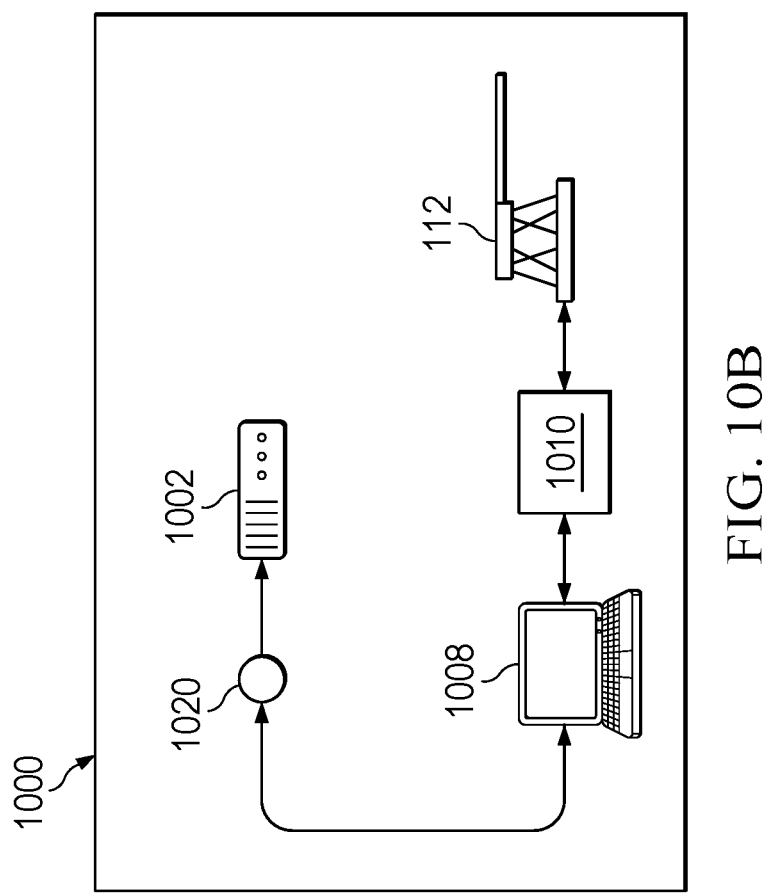

FIG. 10B illustrates RTMM system 1000, according to a further embodiment.

RMMM system 1000, as disclosed above, may comprise primary system 1002, network 1020, computer 1008, controller 1010, and robot 112. In one embodiment, RTMM system 1000 receives output data comprising patient location and/or tracking data from primary system 1002. Data may be sent over network 1020 via a wired, or wireless communication link, as disclosed above. Computer 1008 receives patient location and/or tracking data and calculates a new position of robot 112 to correct movement of patient on the movable surface. Based at least in part and in response to calculating the corrected patient position on the movable surface, computer sends instructions to controller 1010, which are received by robot 112 to move to a new position. Robot 112 may then send status information back to controller 1010 and/or computer 1008.

Figure 11:
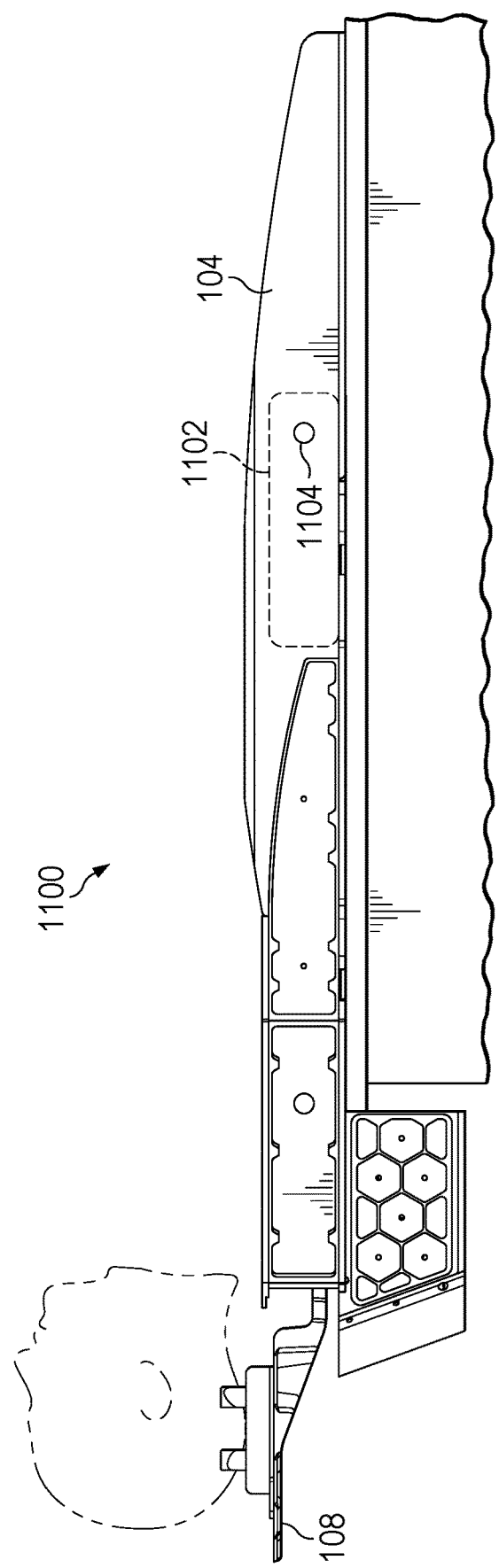
FIG. 11 illustrates the battery-powered movement correction couch overlay, according to an embodiment.

FIG. 11 illustrates a battery-powered movement correction couch overlay 1100, according to an embodiment. To provide greater flexibility and reduce the amount of cable clutter, movement correction couch overlay 100 may comprise battery pack 1102 and charging port 1104 to power movement correction couch overlay 100. In one embodiment, battery pack 1102 of battery-powered movement correction couch overlay 1100 is located under the patient support cushion 104. Battery pack 1102 provides for movement correction couch overlay 1100 operation without connecting to external wall outlets or other external power sources during battery-powered operation. Embodiments contemplate optionally connecting battery-powered movement correction couch overlay 1100 to an external power source during operations to preserve the charge of battery pack 1102 for periods when it is not practicable to connect with an external power source. In addition, or as an alternative, a battery is located and sized (comprising any suitable number of cells of any suitable capacity) such that the weight of the battery back reduces or eliminates the number or weight of the optional counterweights or current mass to keep movement correction couch overlay 100 stable on the treatment coach.

As disclosed above, RTMM system 1000 receives target location information from one or more remote or local imaging devices or visual output from primary system 1002. In one embodiment, RTMM system 1000 receives visual output from primary system 1002 using capture device 1006, which may couple to a video output port from primary system 1002, using one or more adapters, according to particular needs. In one embodiment (and as described in further detail below), RTMM system 1000 utilizes screen reader module 1024 to interpret the visual output of a computer display and retrieve target information (such as, for example, textual, numerical, graphical, or the like) from the visual output. Screen reader module 1024 may be coupled with interpreter 1020, which varies or may be differently configured depending on the type of data which is interpreted, and according to particular needs, as described in further detail below.

Video Capture Method

The video capture method of data collection that is used as data input for correction action by RTMM system 1000 by using a video-capture device 1006 to access and process live-video output from a video output of a target device (such as, for example, primary system 1002) by detecting the individual values and translating the detected value into signals controlling robotic functions and logging. In some embodiments, capture device 1006 accesses a video feed by splitting the video signal between primary system 1002 and its corresponding display monitor. In addition, or as an alternative, capture device 1006 accesses the video feed of primary system 1002 by directly connecting to an outgoing video cable on a computer controlling primary system 1002. Embodiments further contemplate capture device 1006 comprising an imaging sensor directed to an output device (such as, for example, a monitor), which transmits a live-video feed from primary system 1002 to RTMM system 1000.

Although RTMM system 1000 is described as receiving patient monitoring data from splitting or duplicating an output signal from primary system 1002, embodiments contemplate RTMM system 1000 receiving data from other media types by providing other suitable interpreters 1020, as described in further detail below. In addition, or as an alternative, data may be collected from one or more auditory inputs (e.g., sounds, voices, ambient noise, static, audio channel of primary system output, and the like), wireless signals, radiation, and the like. Embodiments further contemplate verifying the received data to identify the received data and to avoid incorrect interpretation and results. Further embodiments contemplate RTMM system 1000 receiving patient position data from an imaging system that transmits patient position data to RTMM system 1000. The imaging system may comprise one or more cameras to track a patient in real time. The imaging system may include a closed system that sends data to the couch overlay's designated receiver for processing and utilization.

Figure 12:
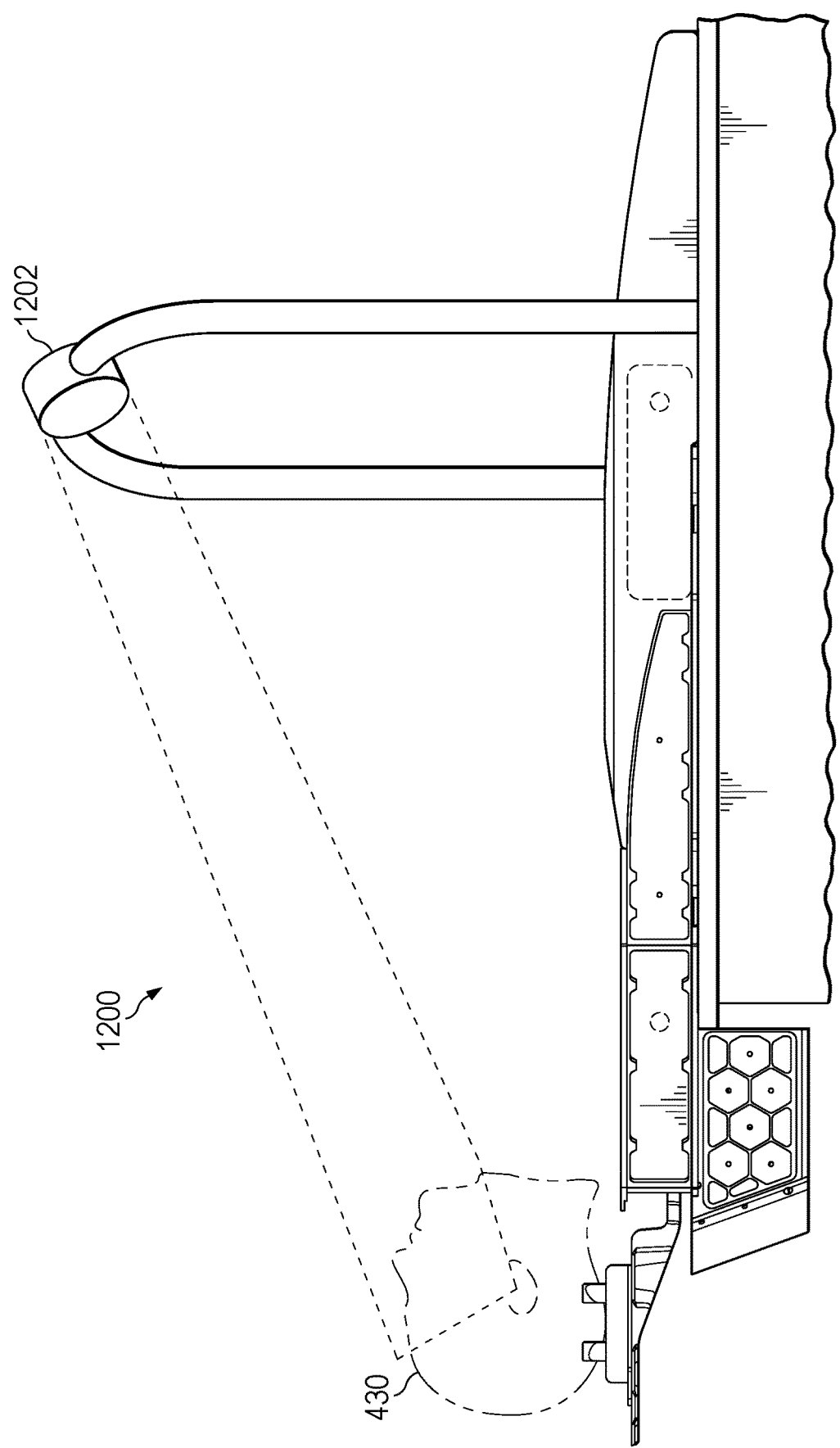
FIGS. 12-13 illustrate imaging systems, according to embodiments.

FIG. 12 illustrates imaging system 1200, according to a first embodiment.

Imaging system 1200 comprises imaging device 1202. Imaging device 1202 comprises one or more imaging sensors to observe the patient (here, represented by phantom head 430), tracking changes in position through methods such as calculating target position relative to highly reflective points placed on the patient, analyzing/tracking the surface geometry of the head, or using continuous x-ray scans of the patient during treatment.

Figure 13:
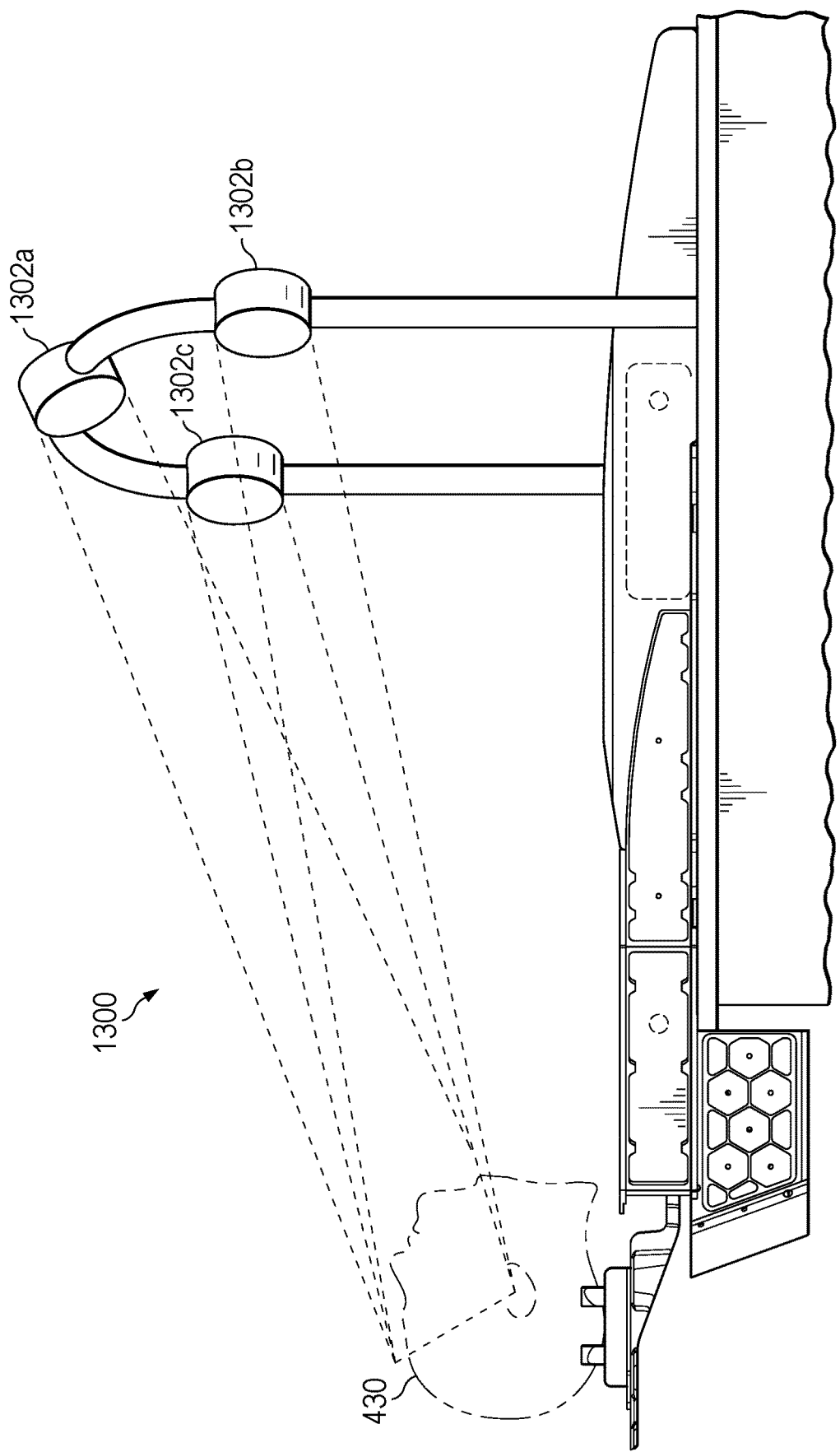

FIG. 13 illustrates imaging system 1300, according to further embodiment. Imaging system 1300 may comprise any number of one or more imaging devices 1302a-1302c having one or more sensors, processors, and memory, and may include any suitable input device, output device, fixed or removable computer-readable storage media, or the like. According to embodiments, one or more imaging devices 1302a-1302c comprise an electronic device that receives data from one or more sensors or from one or more data storage locations. One or more sensors of one or more imaging devices 1302a-1302c may comprise an imaging sensor, such as, a camera, scanner, electronic eye, photodiode, charged coupled device (CCD), or any other electronic component that detects electromagnetic radiation or visual characteristics (such as color, shape, size, location, orientation, or the like) of objects. One or more imaging devices 1302a-1302c may comprise, for example, a networked electronic computing configured to image patients using one or more sensors and transmit patient location or movement data to RTMM system 1000.

One or more imaging devices 1302a-1302c may generate a mapping of the patient location or movement by scanning a visual field that includes the patient and/or movement correction couch overlay 100. This may include, for example, a stationary scanner located at one or more locations within the treatment environment that scans movement correction couch overlay 100 and patients within the field of view. As explained in further detail below, RTMM system 1000 may use the mapping of phantom head 430, patient, movement correction platform, and the like to locate a treatment location, a patient, an isocenter, or like visual target. The location of the patient or other visual target may be used by RTMM system 1000 to move a movement correction base in a direction to counter any movement by a patient. In addition or as an alternative, one or more sensors of one or more imaging devices 1302a-1302c may be located at one or more locations local to, or remote from, one or more imaging devices 1302a-1302c, including, for example, one or more sensors integrated into one or more imaging devices 1302a-1302c or one or more sensors remotely located from, but communicatively coupled with, one or more imaging devices 1302a-1302c. According to some embodiments, one or more sensors may be configured to communicate directly or indirectly with RTMM system 1000, one or more computers, and/or the network using one or more communication links.

Capture device 1006 transmits capture data 1048 to computer 1008. In one embodiment, capture data 1048 from capture device 1006 or imaging system 1300 is received by the designated receiver. RTMM system 1000 interprets captured information and calculates a new position. The calculated position of robot 112 is determined based on deviation of known position from the target position, which can be determined by internal anatomy obtained from imaging such as CT scans, MRI, and the like, as disclosed herein. In addition, or as an alternative, the target position is determined by RTMM system 1000 by external anatomy through imaging methods such as surface tracking of the face or other external anatomy features. The resulting movement path and velocity are additionally controlled by defined limits and restrictions determined for the purpose of safety and mechanical constraints and limitations with respect to the patient's wellbeing. Adjustments to the path and velocity may be implemented by user input, as described in further detail below.

Computer 1008 sends new instructions to controller 1010, and robot 112 receives instructions and moves to its new position, sending status information back to controller 1010. As disclosed above, handler module 1022 may monitor and direct robot 112. Handler module 1022 may further attempt to automatically recover from minor errors and alert the user if a more serious fault occurs. According to embodiments, handler module 1022 monitors and directs robot 112. Embodiments of handler module 1022 serve as the intermediary between screen reader module 1024 and robot controller module 1026.

Phantom Head for RTMM Treatment Device

Figure 14:
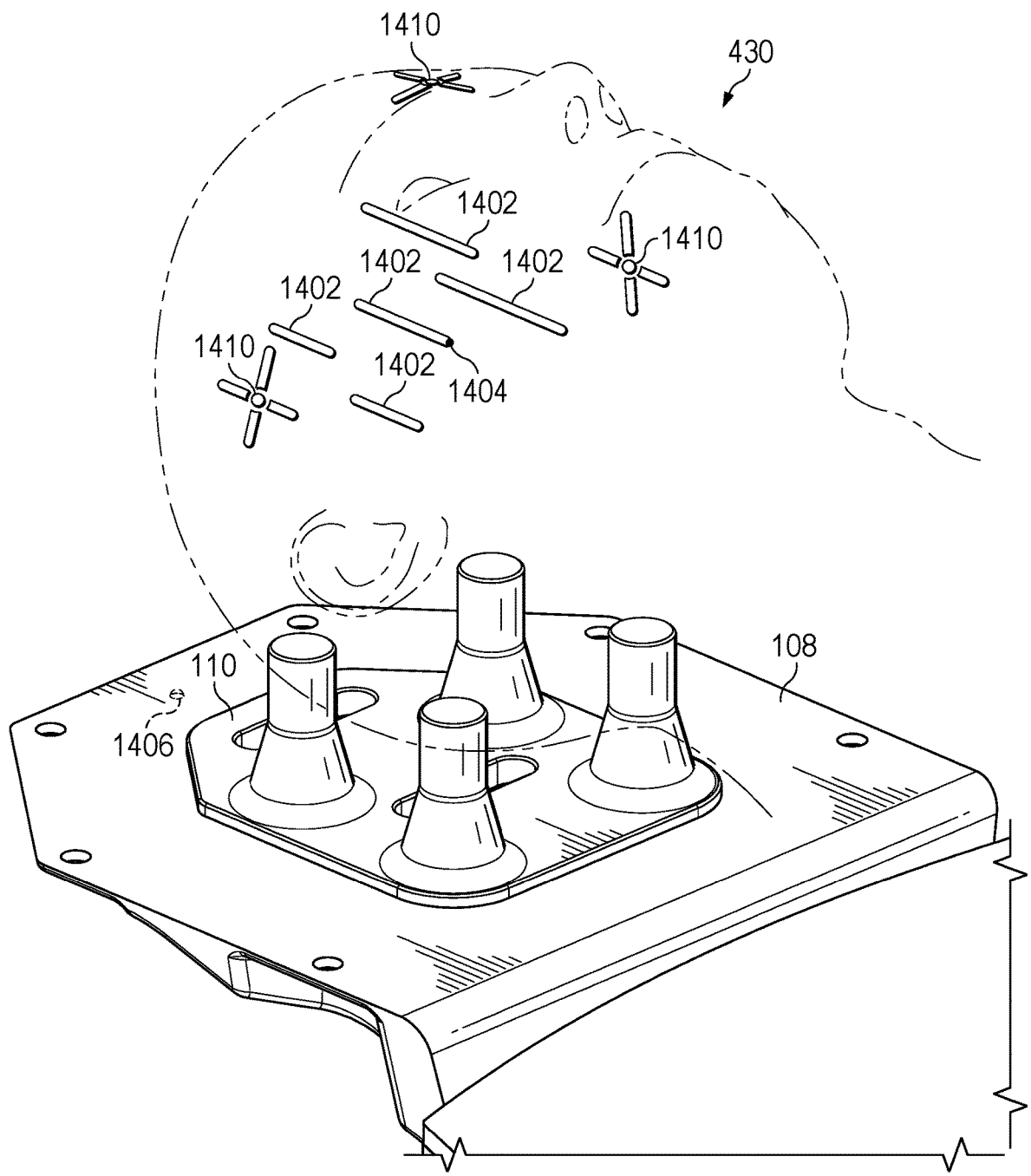
FIG. 14 illustrates the phantom head, the base headboard, and the headrest attachment, according to an embodiment.

FIG. 14 illustrates phantom head 430, base headboard 108, and headrest attachment 110, according to an embodiment. In the illustrated embodiment, phantom head 430 model comprises a low-density plastic simulacrum of a human head for the purpose of calibrating and testing equipment for radiotherapy. Phantom head 430 model may comprise two main sections manufactured to interlock into one another and remain affixed with a single MR safe screw located at the top of the head. However, phantom head 430 model may comprise any number of one or more sections and be coupled with any suitable coupling mechanism, according to particular needs.

In one embodiment, phantom head 430 model is produced through additive manufacturing using a Fused Deposition Manufacturing (FDM) device (or other 3D-printer) using thermoplastics or thermosetting plastics. Embodiments further contemplate constructing phantom head 430 model using traditional manufacturing methods, such as, for example, machining, molding (e.g. injection molding), and other like techniques, according to particular needs. According to the illustrated embodiment, phantom head 430 model comprises a hollow interior, with a minimal quantity or amount of supportive structures needed to maintain integrity of the model during normal usage, as disclosed herein. In addition, the inside of phantom head 430 model may comprise a quantity of shafts 1402, containing within high-density spheres 1404 which are sized and configured to contrast with the primary construction material of the head. By way of example only and not by way of limitation, a single high-density sphere 1404 may be located at the bottom of one or more shafts 1402. In addition, or in the alternative, the spheres may be encapsulated in the head by a molding-in technique, which eliminates the need to place shafts 1402 within the model. As described in further detail below, high-density spheres 1404 are used as isocenter points and serve as an analogue to tumor locations in a patient's head, allowing phantom head 430 model to be used as a uniform test case for calibrating and testing equipment in a treatment setting. Base headboard may comprise an isocenter location anchor 1406. Although the high-density spheres are described as spheres, embodiments contemplate any suitable shape, according to particular needs. Sphere materials typically consist of steel or tungsten but can potentially be substituted with any suitably dense material if required due to situational restrictions such as use in MR environments.

In one embodiment, the outer surface of phantom head 430 comprises target markings 1410 that provide for alignment of beams (such as, for example, those utilized for CT scans) with phantom head 430 to calibrate and test RTMM system 1000. In addition, embodiments of phantom head 430 comprise a quantity of apertures or indentations located on the occipital or dorsal surface which may be used to receive corresponding mounting members from a mounting adapter to secure phantom head 430 to a fixed position and orientation with respect to base headboard 108 and/or headrest attachment 110 to provide for repeatable test cases. Although the illustrated embodiment of phantom head 430 comprises a hollow interior with high-density targets located in shafts 1402, embodiments of phantom head 430 may comprise a density, weight, configuration, and/or radiological appearance by construction of materials that simulates an anatomically correct model of a human head, such that it simulates an optic chiasm, brain stem, brain tissue, brain cavity, bones, skin, cartilage, teeth, or other like anatomical features and may be constructed of tissue-equivalent materials. The high-density targets may be located in any suitable target locations within the anatomical phantom head 430. Embodiments further contemplate variants of phantom head 430 for various head shapes, various and differently located and configured markings for any suitable alignment or tracking system, and phantom head 430 model that provides for placing weight within the internal cavity to simulate various masses of human heads, which may be used for load-testing RTMM system 1000.

Figure 15:
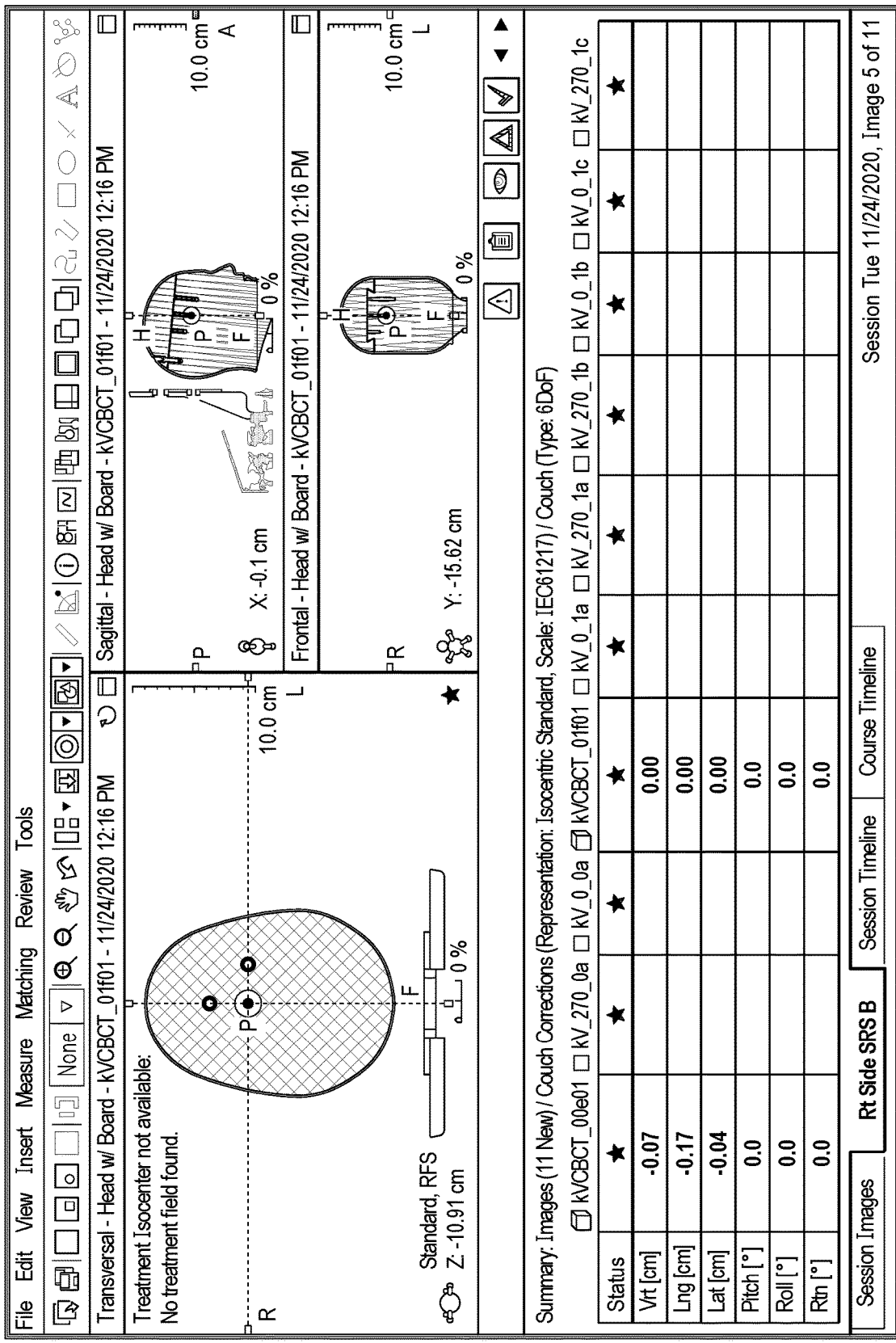
FIG. 15 illustrates frontal, sagittal, and transversal cone beam CT scan of the phantom head, according to an embodiment.

FIG. 15 illustrates frontal, sagittal, and transversal cone beam CT scan 1500 of phantom head 430, according to an embodiment. As disclosed above, RTMM system 1000 receives a video output from a primary patient movement monitoring system. RTMM system 1000 may capture the video feed using capture device 1006 and transmit the video feed to computer vision system. The computer vision system of capture device 1006 reads and displays the video feed, followed by processing the feed to obtain pertinent information regarding the patient's deviation from the target position or other displayed information.

Capture Process

Upon establishing a connection with capture device 1006, RTMM system 1000 may begin to process the incoming video data frame by frame. Prior to its primary use as a component of RTMM system 1000, capture module 1028 may be adjusted using a series of configuration tools. These configuration tools allow the module to be tuned to best utilize a specific computer's visual output and include: defining Regions of Interest for data capture of areas with pertinent information (selecting the numbers or output to read); training the module's character recognition tool to recognize new font types and characters as needed; and defining a set of validation templates 1046 used to assess the validity of the interpreted values to mitigate and catch potential errors in the capture results. These configuration tools provided for RTMM system 1000 and methods of their operation are described in further detail below. Embodiments provide screen reader module 1024 initiated as a web service to manage data remotely, as disclosed herein.

Capture module 1028 processes video frames collected by capture device 1006. According to embodiments, capture module 1028 receives the newest frame of the captured video and extracts the pixel data located within defined regions of interest from the captured frame. Capture module 1028 isolates contours from each region to generate a set of contours representing the individual characters found within that region.

Figure 16:
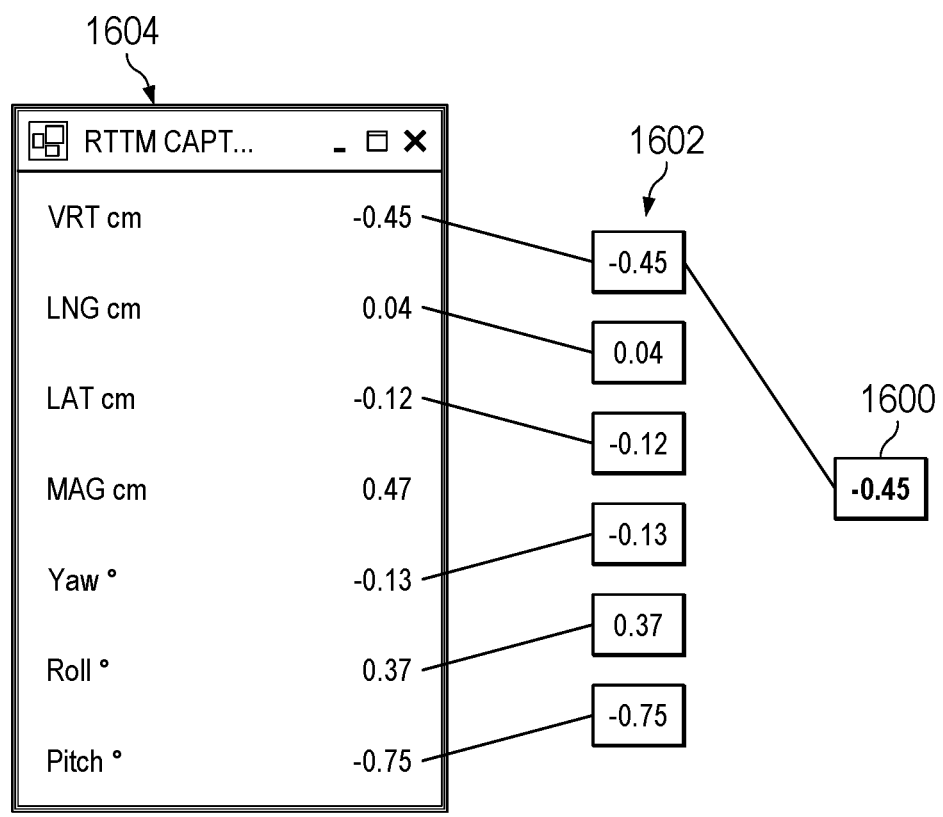
FIG. 16 illustrates a set of contours identified from captured characters, according to an embodiment.

FIG. 16 illustrates a set of contours 1600 identified from captured characters 1602, according to an embodiment. In the illustrated embodiment, capture module 1028 identifies a set of contours 1600 representing captured characters 1602 captured from deviation data display 1604 and preprocesses the contours using a suitable preprocessing method to obtain uniform size and contrast, as described in further detail below. Although a particular preprocessing method is described, embodiments contemplate other suitable data, graphical, textual, and numerical preprocessing methods used to improve optical image/character recognition, according to particular needs.

At a first activity of the illustrated preprocessing method, the character is converted into grayscale. At a second activity, the character is rescaled to best fit a box of predefined dimensions without exceeding said dimensions. At a third activity, the image of the character undergoes a threshold transformation where the greyscale intensity is compared to a predefined threshold. If the value of the pixel is above the threshold it is set to the highest intensity value (255) and if it is below the threshold it is set to the lowest intensity value (0) to create a sharp contrast between the character graphic and the background.

After preprocessing, the character set collected in each region is then passed into an Optical Character Recognition (OCR) module 1030 of RTMM system 1000 to determine the identity of the contours (e.g., the letter/number/symbol represented by the character graphic). The OCR interpretation may then be validated by comparing the processed character image to a stored template that represents a confirmed example of a character graphic (which may be produced during the configuration process, as described in further detail below). In one embodiment, OCR module 1030 compares, pixel by pixel, the greyscale values of the chosen template with the corresponding pixels in the target image. When the number of matching pixels between the template and the target exceeds a given threshold, the OCR interpretation of the character is accepted. When the target fails to match the template, the result is rejected, and the current frame is discarded.

This process of interpretation and validation continues until all samples gathered from a given region have been interpreted. If all characters pass their validation, the resulting textual interpretation of each individual character is then organized based on their position on the captured screen and stored as a text string. This process continues until all regions have been interpreted and the complete result is transmitted to RTMM system 1000.

Configuring Capture Settings

During setup of RTMM system 1000, it may be possible that the capture is slightly misaligned, or the results of the capture are rejected by RTMM system 1000 due to a difference in resolution or video quality from one display configuration to the next. RTMM system 1000 provides a series of capture utilities to help configure the capture settings to obtain the proper results from the capture target. The utilities include tools that assist with defining capture targets, training the system to recognize the characters captured in those regions, and defining a template set used to validate the results produced by capture module 1028 to improve accuracy. In one embodiment, changes made through these tools will take effect on the next run of RTMM system 1000. Embodiments contemplate providing real time dynamic adjustment of these properties.

Region Selection: Defining the Capture Region

Configuration module 1032 defines a focus and targets. To reduce the time needed to collect capture data 1048, RTMM system 1000 uses a defined set of regions, only rendering what is within a capture region and ignoring the rest of the captured scene.

Figure 17:
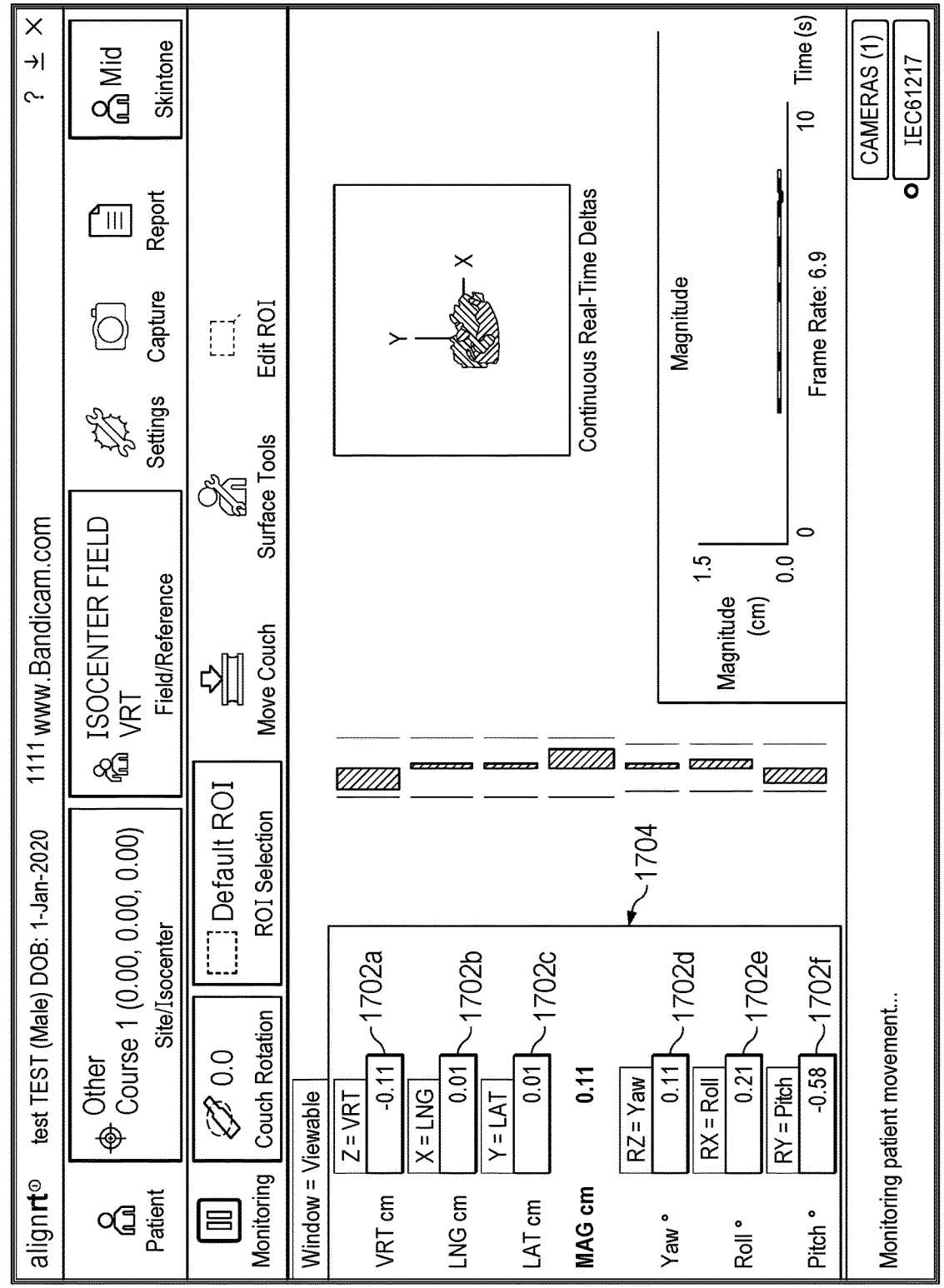
FIG. 17 illustrates a defined region set of patient tracking video capture, according to an embodiment.

FIG. 17 illustrates a defined region set of patient tracking video capture 1700, according to an embodiment. According to the illustrated embodiment, RTMM system 1000 generates a video capture of patient tracking system and provides a user input or selection interface to define a region by an area of the screen that corresponds to a pertinent piece of data, such as, for example, deviation data for a movement or direction. The selection process may be facilitated by a user input device (e.g., a computer mouse, touchscreen, or the like), which repeats until the values for each of the six directions of movement have been selected. According to embodiments, RTMM system 1000 displays prompts to associate each direction with a particular selected region. Video capture 1700 displays target deviation data as numerical values associated with six directions. The target deviation data is selected as the defined region set, with one selection region 1702a-1702f for each of the six potential types of target deviation currently being tracked, with a name tag identifying what type of robot movement is used to correct said deviation. Additionally, a seventh selection box 1704 may be utilized to encompass the other six selected regions 1702a-1702f, which represents the section of the captured screen displayed when RTMM system 1000 is running in capture mode. In one embodiment, RTMM system 1000 displays the area selected around the six major regions. However, to increase this viewable area, RTMM system 1000 provides for defining an additional region called the 'Viewable Region' that dictates what part of the screen will be displayed in the capture window of the system's control panel. Once the regions have been defined RTMM system 1000 may then store the results, which can later be used for additional configuration setup and for movement correction by RTMM system 1000.

Character Trainer: Training the System to Read a New Font Type

According to embodiments, RTMM system 1000 receives confirmation that the defined regions correctly recognize the text being captured. In these embodiments, RTMM system 1000 may display a prompt to provide a region set generated by the region selection tool. The capture window will then open, displaying the targeted regions, the direction associated with each region, and the value the capture system has assigned to that region based on the detected text within the given region.

Figure 18:
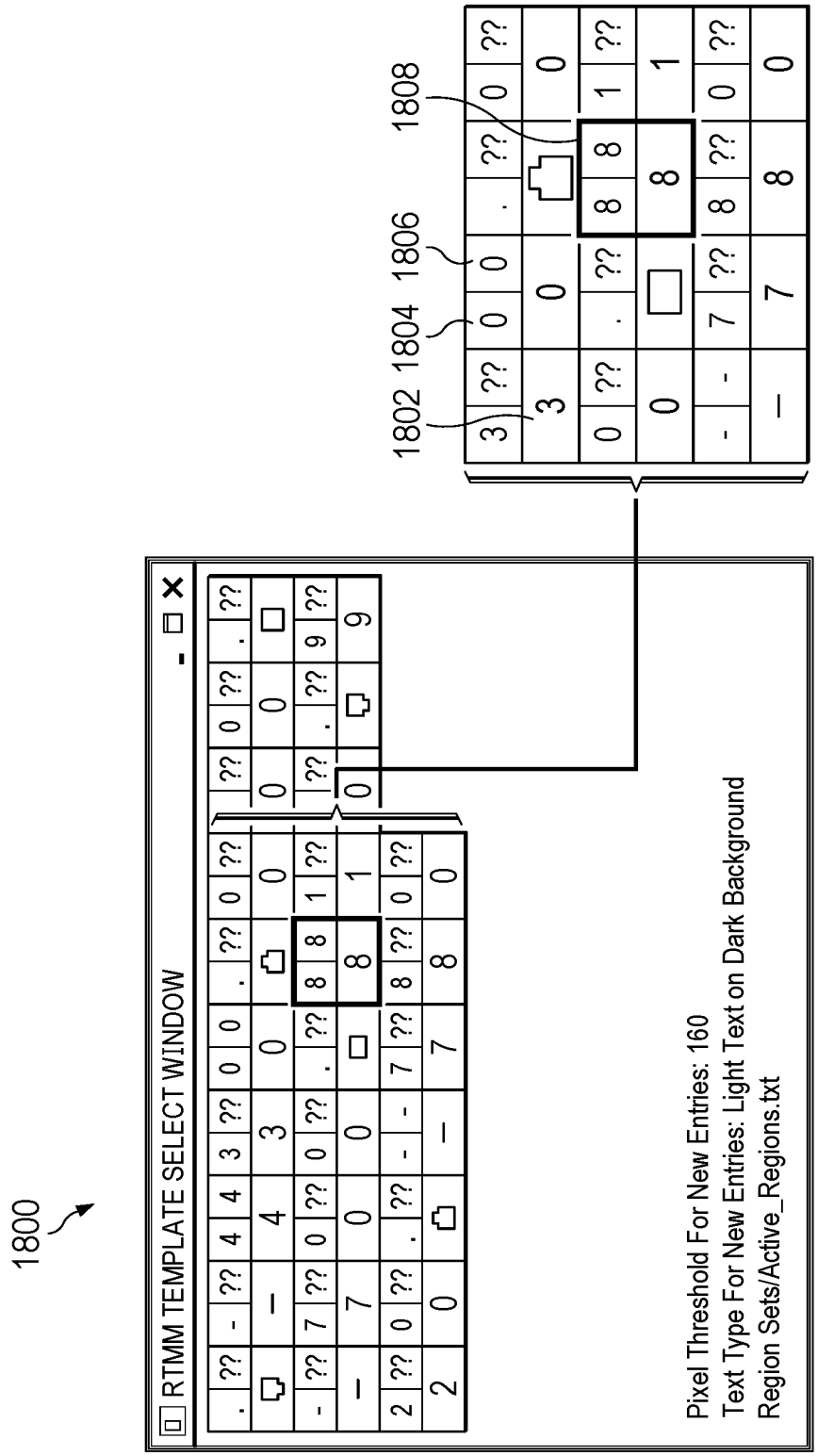
FIG. 18 illustrates a window of the trainer module, according to embodiment.

FIG. 18 illustrates window 1800 of trainer module 1034, according to embodiment. Window 1800 of trainer module 1034 displays the individual characters captured by the system in a grid format. Each cell of the grid includes the character being read (captured character 1802), the interpretation of the character's value by RTMM system 1000 (assumed value of capture 1804), and a user-set value for the actual value of the character (user-assigned value 1806). RTMM system 1000 provides for user navigation of the grid using navigation box 1808 and setting the value for a given cell by entering the correct result for the given character. Cells not manually set by the user may be assigned a value of '??' and are ignored by the system for training purposes. Once the assessment of the captured text is finished, RTMM system 1000 may upload feedback to knowledge base 1040 of RTMM system 1000. In one embodiment, knowledge base 1040 provides for improving recognition of the character set during training. Once the system has reached a predetermined level of accuracy, RTMM system 1000 may store the new character recognition set 1042 for later use.

Validation Set: Creating a Validation Character Set

Once the regions have been defined and the character recognition updated, the next activity comprises generating validation character set 1044. Validation character set 1044 is used by RTMM system 1000 to generate validation templates 1046 used to verify each character read by the system to validate the results of the capture. In an embodiment, RTMM system 1000 displays an option of selecting character recognition set 1042 and designated capture regions to be used in the process. In addition or as an alternative, RTMM system 1000 automatically builds a validation set based on the loaded text interpreter 1020 and displays the results on the top of the display window. RTMM system 1000 may provide for navigation of the template listing and selection or rejection of specific validation templates 1046. Rejected templates may then be deleted and replaced with the next suitable character captured by RTMM system 1000.

Figure 19:
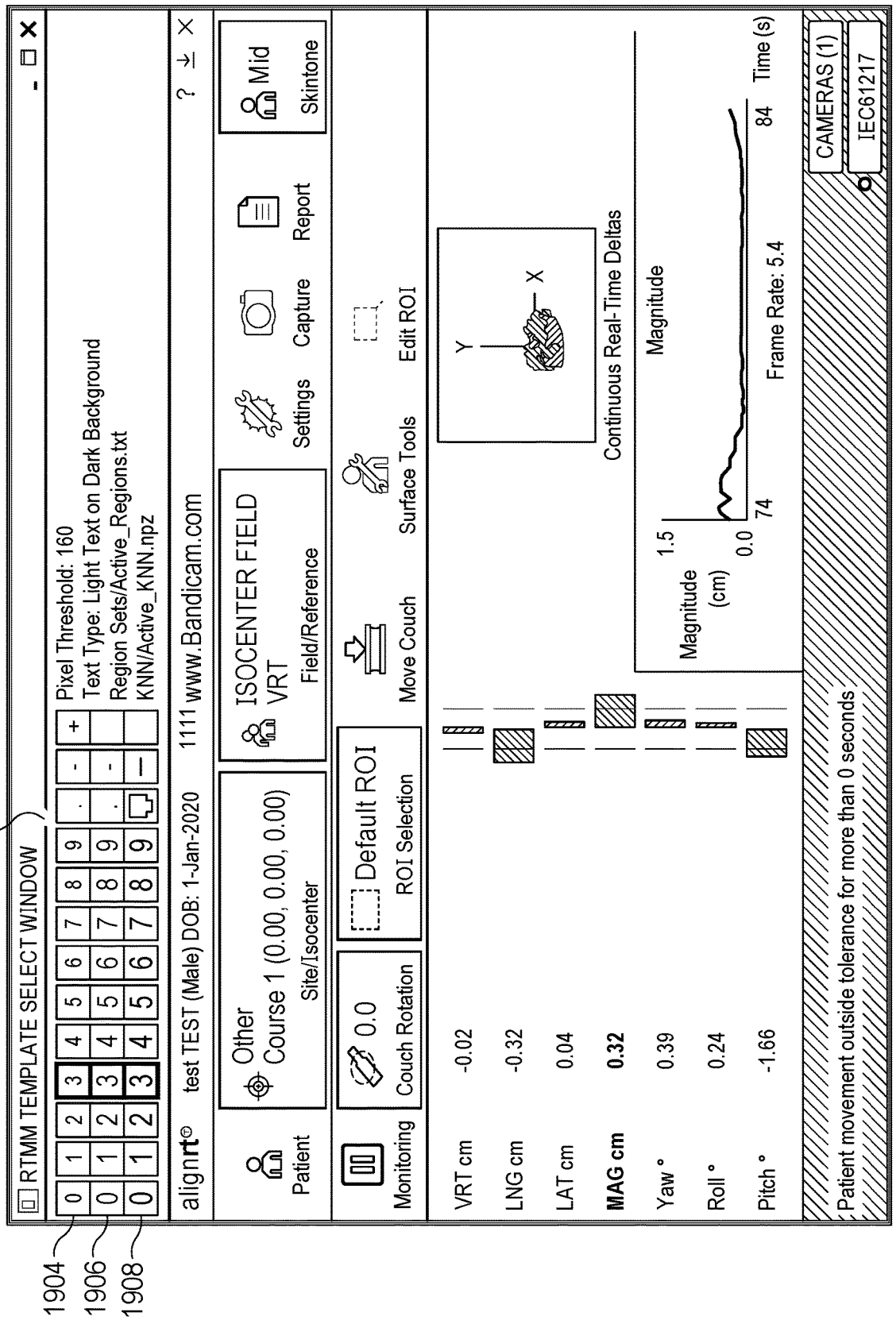
FIG. 19 illustrates an automatically generated template collection derived from monitored video capture, according to an embodiment.

FIG. 19 illustrates an automatically generated template collection derived from monitored video capture 1900, according to an embodiment. Table 1902 illustrates, in descending order, the text 1904 represented by the template, the collected sample 1906 used to generate the template, and the final template render 1908 to be used by RTMM system 1000 for text validation. Once validation templates 1046 are deemed acceptable, RTMM system 1000 stores the results for later use.

Manual Versus Automatic Control Modes for RTMM System in Capture Mode

According to embodiments, manual and automatic position control modes provide different functionality. While in automatic correction mode, RTMM system 1000 will move robot 112 based on the provided capture data 1048 and manual movements are ignored until the stop button is pressed. While in manual movement control mode, RTMM system 1000 will only move robot 112 in response to user input to adjust position with the available manual movement controls. Capture data 1048 may still be viewable in this mode but may not affect movement.

Manual Mode Control Panel

According to embodiments, manual mode comprises a basic mode of operation for RTMM system 1000 by providing the user with tools to adjust a patient's position with no capture data 1048 presented or used. While in this mode, RTMM system 1000 provides for adjusting the isocenter, monitoring the system's overall position, and moving the patient into a new position relative to the active isocenter.

Figure 20:
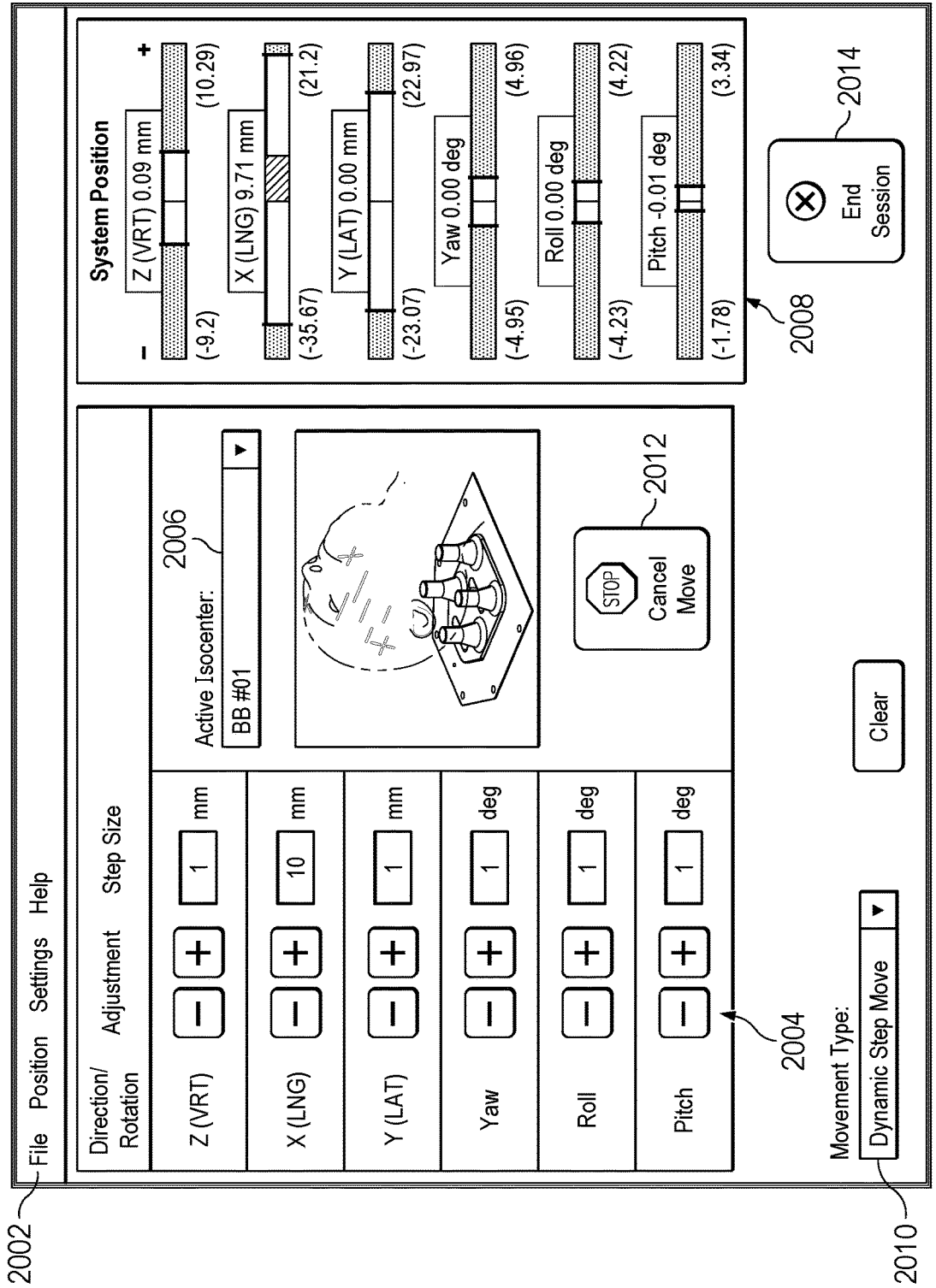
FIG. 20 illustrates the manual control panel, according to an embodiment.

FIG. 20 illustrates manual control panel 2000, according to an embodiment. Manual control panel 2000 comprises a user interface having interactive graphical elements that provide control and monitoring of repositioning of the patient. In the illustrated embodiment, manual control panel 2000 comprises tool bar menu 2002, manual movement controls 2004, isocenter selection menu 2006, system position graph 2008, end session button 2010, cancel move button 2012, and movement type selection menu 2014.

According to an embodiment, manual movement controls 2004 comprise interactive graphical elements comprise buttons that translate and rotate the patient's head position about the vertical, lateral, and longitudinal axes. For the manual movement controls 2004 for the illustrated dynamic step movement mode, user selection of negative direction step button and/or positive direction step button increases or decreases the value of the corresponding direction (z/vertical, x/longitude, y/latitude) or rotation (yaw, roll, and pitch). In response to (and/or based at least in part on) the user selection using the movement type selection menu 2010, RTMM system 1000 provides three primary methods of manual movement: dynamic step movement, relative movement, and corrective movement, as described in further detail below.

For the movement manual controls for dynamic step movement action input of manual control panel 2000, RTMM system 1000 adjusts the patient's position in a single direction using adjustable step-sizes. According to an embodiment, step size is a user-selected amount that is received by RTMM system 1000 using step size input box. According to an embodiment, the user-defined step size is set by receiving a user input of a step size magnitude in an input box. By way of example only and not by way of limitation, pressing the + button may move the patient by the given step size in the positive direction and the – button will conversely move the patient in the negative direction. According to an embodiment, only a single direction (positive or negative) move may be accepted while in dynamic step move mode.

System position graph 2008 provides visualization and tracking of position and mechanical limits of motion correction couch overlay 100. According to embodiments, this visualization indicates, for each direction, the current position relative to its neutral starting position relative to the current active isocenter. System position graph 2008 displays direction name and position value, maximum step size, limit of motion, and current position relative to limits. In addition, system position graph 2008 displays the maximum step that can be made from the current position in both the positive and negative directions, providing for planning subsequent movements. As a certain direction or rotation changes, a bar representing that movement approaches the vertical lines at each end of the graph, allowing the user to quickly note upcoming limits and restrictions on their movements. When a certain value reaches its limit, its corresponding bar may turn from one color to another (such as, for example, from green to red) to illustrate the inability to move further in the given direction.

FIG. 21 illustrates an example movement direction reference 2100, according to an embodiment. As seen by reference to the above illustration, a positive and negative direction may be set for each of the three translational directions 2102-2106 and three rotational directions 2108-2112 for movement of RTMM system 1000 (indicated by the arrows associated with each of the head models). Although example movement direction reference 2100 is shown in a particular embodiment, other embodiments may assign positive or negative to either orientation or assign any suitable label to any of the axes, directions, or rotations, according to particular needs.

FIG. 22 illustrates relative movement input 2200, according to an embodiment. When relative movement is selected from movement type selection menu 2010, manual control panel 2000 displays relative movement input 2200. Unlike movement manual controls 2004 of manual control panel 2000, when adjustment to direction or rotations are input using relative movement input 2200, all of the input movement adjustments are sent to robot 112 at once. While in the relative movement mode, movement input entry boxes receive user inputs for all desired adjustments. After all of the adjustments are input to relative movement input 2200, a user may select a "submit" button. In response to selection of the submit button, RTMM system 1000 sends instructions to move robot 112 from its current position according to the input values for each of the movement adjustments. When corrective movement is selected from movement type selection menu 2010, RTMM system 1000 displays corrective movement action visualization. Corrective movement compensates for a known positional deviation. While in corrective movement mode, in response to RTMM system 1000 receiving input indicating that the target has deviated from the ideal position, RTMM system 1000 calculates and adjusts robot 112 to move in the opposite direction of the entered values to correct the deviation.

Capture Mode Movement Controls

Figure 23:
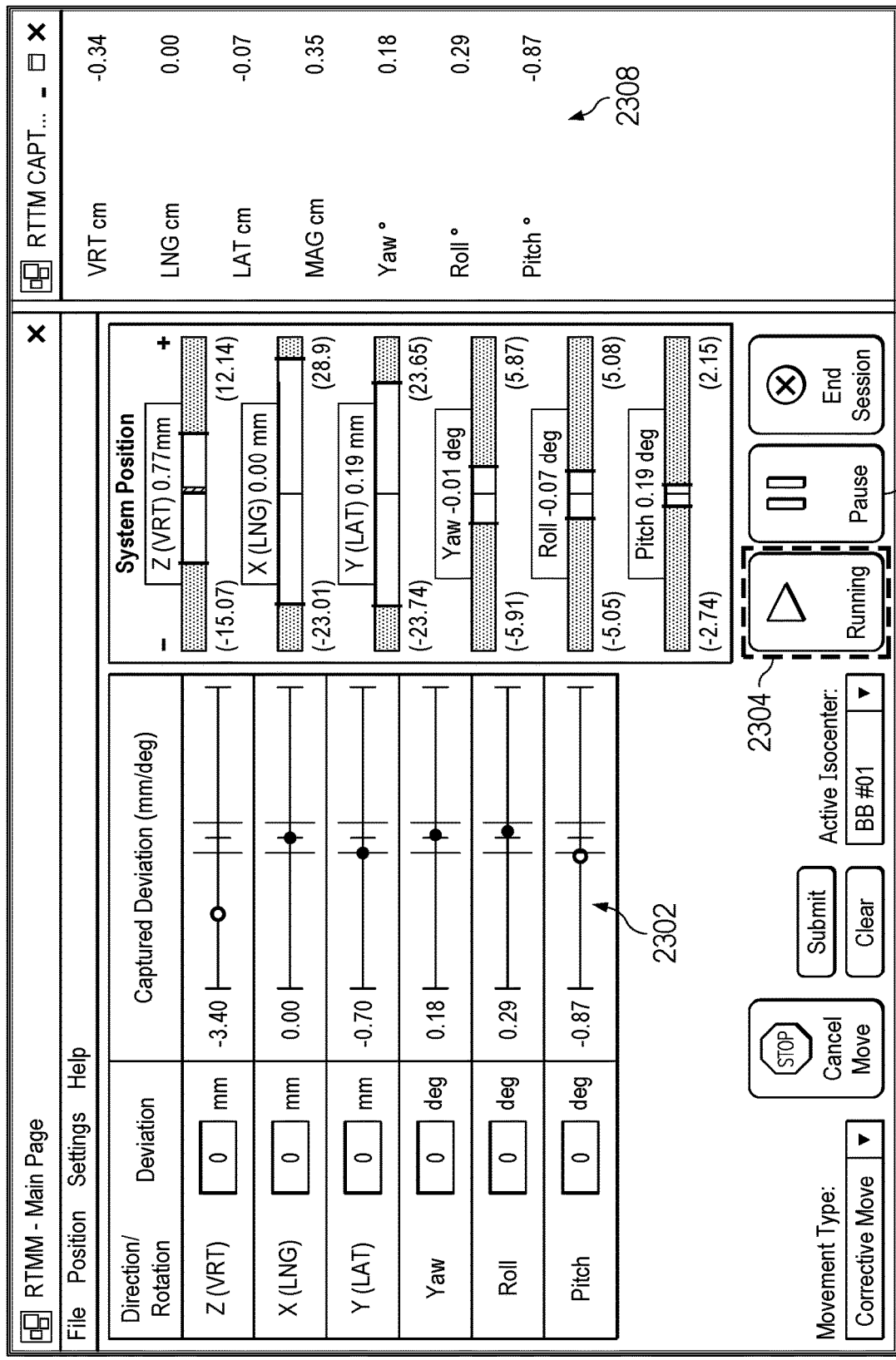
FIG. 23 illustrates the capture mode control panel, according to an embodiment.

FIG. 23 illustrates capture mode control panel 2300, according to an embodiment. Capture mode control panel 2300 provides some similar functionality as manual mode control panel 2000 but includes additional controls for incorporating video data collected from a monitor or input source. As described in further detail below, these additional controls may provide a visualization of the patient's deviation relative to the current tolerance and the ability to set RTMM system 1000 to automatically correct the patient's position based on the data collected by capture module 1028.

According to an embodiment, capture mode control panel 2300 comprises deviation monitor graphs 2302, automatic correction start button 2304, automatic correction pause button 2306, and screen capture display window 2308. In one embodiment, RTMM system 1000 automatically adjusts the patient's position based on its current deviation from the target position when RTMM system 1000 is set to capture mode. Deviation monitor graphs 2302 comprise visualizations of the amount of deviation detected from the patient's target location as read by capture module 1028 of RTMM system 1000. RTMM system 1000 may activate capture mode in response to receiving a user selection of the automatic correction start button 2304. When automatic correction is active, a border may be placed around this button and the text may change to "Running". In addition, or as an alternative, RTMM system 1000 ends capture mode in response to user selection of automatic correction pause button 2306 and halts any active movement. Capture model control panel 2300 may comprise various control buttons and possible states, according to particular needs. By way of example only and not by way of limitation, when automatic correction is unavailable due to an error or issue, the system may prevent starting the automatic correction and may display the text "Capture Error." By way of a further example, while in the capture mode, the RTMM the system may move based on the provided capture data 1048 and prevents manual adjustments until automatic correction pause button 2306 is selected. In addition, or as an alternative, when the automatic correction pause button 2306 is selected, RTMM system 1000 may only move when the user directly adjusts its position with manual movement controls.

According to embodiments, deviation monitor graphs 2302 comprise deviation trackers for each direction (z/vrt, x/lng, y/lat, yaw, roll, and pitch). Each of the deviation trackers may comprise a current deviation, deviation value, target position, and tolerance limit. The current deviation for each direction is displayed by indicators and deviation value. In one embodiment, the indicators comprise an icon (here, a circle) that represents the magnitude of the tracked deviation in either the positive or negative direction. The greater the deviation, the further away the indicator will move from the center point of the deviation tracker. The two vertical bars along each tracker bar represent the set tolerance range for that corresponding direction. When this tolerance is exceeded the tracker ball may turn from a first color to a second color, indicating a need for correction on that axis of movement. The number located to the left of the tracker bar represents the deviation value collected from the display currently being captured. These values are measured in millimeters and degrees depending on the type of positional data it is tracking (millimeters for translation, degrees for rotation). In addition, or as an alternative, RTMM system 1000 provides the option to track the combined deviation magnitude across the vertical, longitudinal, and lateral axes. The combined deviation magnitude tracker detects when the combined deviation across the three translational axes exceeds a set threshold, providing greater control over deviation management. Embodiments further contemplate using machine learning and optimization through data analysis to, for example, anticipate, optimize, adjust, and correct movement and the like.

Coordinate System

In one embodiment, RTMM system 1000 provides an internal coordinates system that determines movement in a three-dimensional space anchored around a fixed anchor point. Embodiments of RTMM system 1000 provide for alignment of movement correction couch overlay 100 with a patient's targeted treatment area. According to embodiments, the coordinates system of RTMM system 1000 utilizes a tungsten ball embedded in an edge of base headboard 108 as a fixed anchor point. In response to (and based, at least in part, on) a user input to modify one or more coordinates settings, RTMM system 1000 aligns a patient's treatment area relative to the fixed anchor point. RTMM system 1000 centers its movement around the modified anchor point. Values are entered with respect to the selected coordinate system, and embodiments contemplate any suitable units of measurement (e.g., millimeters).

The coordinates settings provide for user input of coordinate values for one or more directions. In response to (and based at least in part on) the user input, RTMM system 1000 displays a visualization comprising an image of base headboard 108 with the anchor point represented by an icon and updates the location of the icon representing the anchor point in accordance with the input values. The input of the updated anchor point coordinates may be input in any suitable measurement units, such as, for example, millimeters, centimeters, degrees, radians, and the like.

Embodiments of RTMM system 1000 provides for adjusting correction speed and correction delay. In one embodiment, RTMM system 1000 provides for adjusting correction speed and correction delay using settings profiles. These configurations can include coordinate isocenter data, general system, (movement speed, correction delay, etc.), axis definitions (Name, order, direction), movement limitations specific to a patient, etc.

Alert and Status Monitoring

According to embodiments, RTMM system 1000 monitors and displays issues regarding robot 112, capture device 1006, and modules of RTMM system 1000 in an alert and status display. Alerts may comprise one or more of the following status types: robot status, capture status, movement status, and mode status. Robot status monitoring identifies states of robot 112 such as alerting the user when robot 112 is moving, idling, or homing itself. Capture status monitors the status of the data collection from the installed capture device, as well as any errors or issues encountered during this process. Movement status indicates whether any of movement directions are restricted or approaching their limit. Mode status indicates the current mode of the system (e.g., manual, automatic, automatic suspension, suspension). When in manual mode, RTMM system 1000 only moves in response to inputs by one or more users. When in automatic mode, RTMM system 1000 automatically adjusts the patient's position based on collected capture data 1048. When in automatic suspension mode, RTMM system 1000 has encountered an issue that prevents automatic correction. When the issue is resolved, RTMM system 1000 will return to automatic mode. When in suspension mode, RTMM system 1000 has encountered an issue that prevents automatic correction but allows the user to manually adjust the patient's position.

RTMM system 1000 may provide a settings interface to modify, for example, profile name field, correction speed control, correction delay control, and magnitude monitor toggle. Profile name field provides for user input of name assignment for a current settings configuration. The stored profiles may then be used to load different configurations of RTMM system 1000, which may be tailored to different operating environments, treatment types, patient preferences, user preferences, and the like. In response to user selection of the previous configuration, RTMM system 1000 applies the settings recorded in the selected profile to RTMM system 1000. Correction speed control adjusts how fast robot 112 moves to correct patient deviation. In one embodiment, the correction speed defaults to 100% as the system's normal speed, but correction speed control provides for manually reducing the speed to, for example, account for patient requiring a more gradual correction rate. Correction Delay Control adjusts the correction delay, which is a user adjustable time delay between the system identifying a deviation and correcting it during an automatic correction session. By increasing the correction delay, RTMM system 1000 accounts for a patient's natural movement to settle before starting a corrective action. The Magnitude Monitor Toggle provides for user selection or deselection of the Deviation Magnitude tracker bar and adjusting its tolerance threshold, as disclosed above. Although settings interface is shown and described as comprising profile name field, correction speed control, correction delay control, magnitude monitor toggle, apply changes button, settings reset button, and cancel button, embodiments contemplate any suitable arrangement of these or other configuration settings, according to particular needs.

RTMM system 1000 may comprise a directions settings interface, according to an embodiment. Directions settings provide for modifying features of movement in a specific direction. Each type of direction/rotation that is controlled by RTMM system 1000 may be modified for one or more of the following movement features: minimum movement range, maximum movement range, minimum tolerance range, maximum tolerance range, and coordinates settings. The movement range is the range of movement between a maximum and minimum that the system can operate in each direction of movement. According to embodiments, RTMM system 1000 detects a current position of robot 112, and when RTMM system 1000 determines robot 112 is outside of a newly adjusted movement range, RTMM system 1000 generates an alert to move robot 112 into the new movement range, cancel the change in movement range before applying these new settings, or select a new movement range that contains robot 112. In addition, the directions settings interface provides for modifying the maximum and minimum of a tolerance range, which is the range of deviation allowed within the system before corrective action is triggered. In some embodiments, coordinate settings provide for adjusting the alignment of RTMM system 1000 with a patient's targeted treatment area which gives greater accuracy in RTMM system 1000's corrective movements.

Embodiments of RTMM system 1000 may utilize adaptive pathing to account for an irregular shape of target area. In one embodiment, regions are defined in a 3D coordinate space and robot 112 receives instructions from RTMM system 1000 to avoid a particular region during a corrective movement (e.g., to prevent the radiation beam from coming into contact with certain sections of the brain for patient safety). In addition, or as an alternative, RTMM system 1000 provides adaptive robotic motion to further accommodate the type of patient movement. By way of example only and not by way of limitation, RTMM system 1000 utilizes one or more AI and/or machine learning algorithms to collect movement patterns as training data along with patient comfort data, movement, and the like to identify certain types of movement that may, for example, require a more gradual or slower robotic device motion in order to provide a more effective or pleasant experience for the patient. Although AI and machine learning models are described as associating patient movement and comfort data with particular movements, embodiments contemplate other suitable associated data and meta-data with particular patient or robotic device movements or positions, treatment regions, and the like to identify prohibited, allowed or movement adjustments according to particular needs. By way of example only and not by way of limitations, adaptive software and machine learning provide learning and optimization through data analysis to predict and alter the movement path of the system to customize and enhance performance and safety for the patient to include, by way of example and not limited to, anticipating movement patterns, optimizing the path of movement with respect to the treatment area, dynamically adjusting parameters based on environmental changes such as noise in the captured data, a shape of the patient, and the like. This may provide for, among other things:

smoother and more gradual movement for slight corrections, including, for example, but not limited to, RTMM system 1000 dynamically adjusts the speed of correction for smaller movements avoid jerky or sudden moves that could startle or cause discomfort in the patient;

tracking movement over time to identify short spikes that could cause over-correction, such as, for example, identifying sudden severe changes in a patient's position that could indicate an agitated patient state that would cause the system to pause its corrections until the patient settles down;

adapting robot movement to accommodate for patient's emotional state, such as, for example, monitoring vitals or breathing to identify situations or certain movements that induce greater stress or discomfort in the patient in order to adjust the corrective movement in an attempt to alleviate a patient's discomfort; and providing less sudden movement for agitated patients, tracking mood and motion to find a custom movement pattern that suits the individual from their previous interaction with the system, and any other combination of these and other use-cases.

Figure 24:
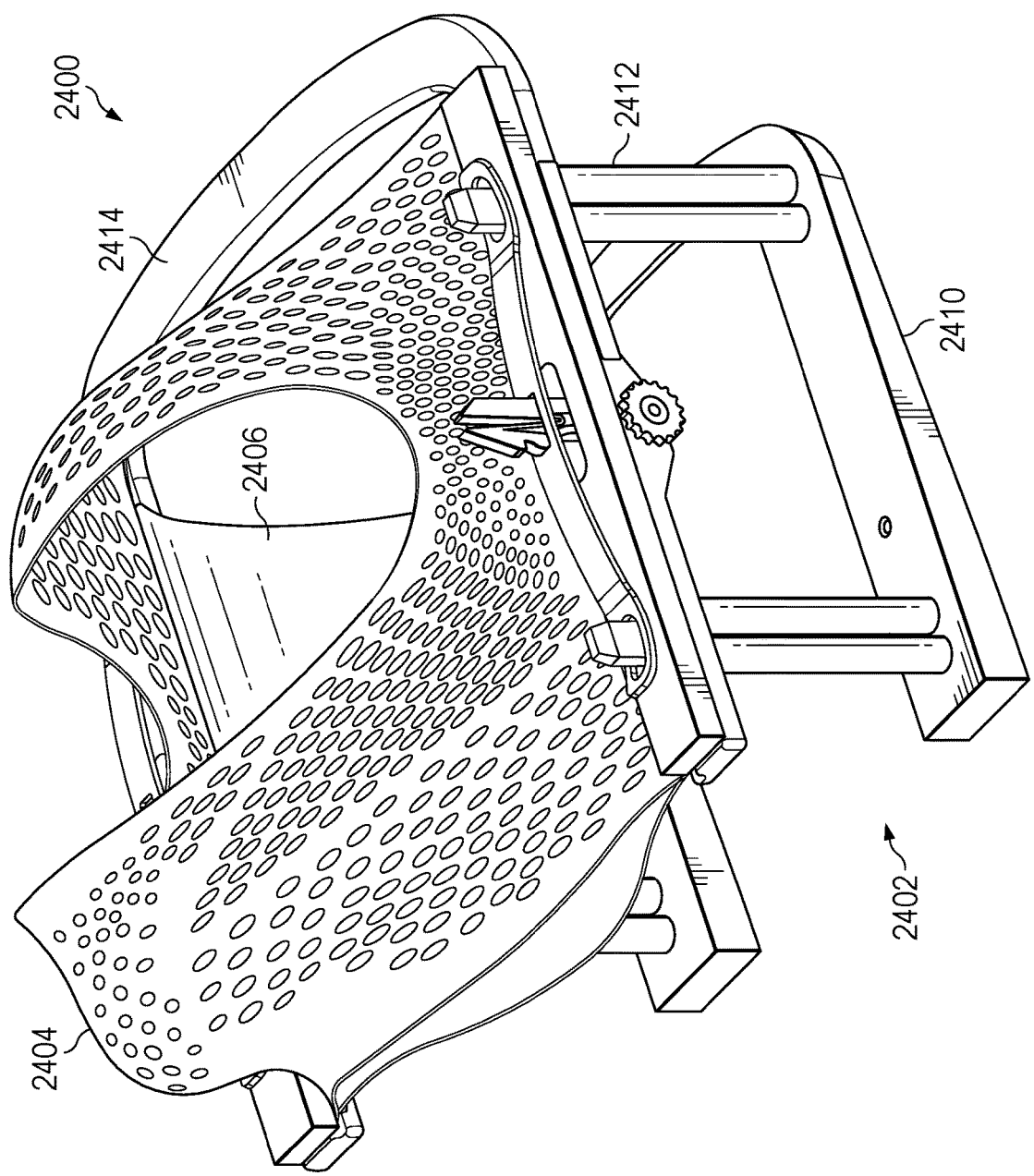
FIG. 24 illustrates the double-mask immobilization device, according to an embodiment.

FIG. 24 illustrates double-mask immobilization device 2400, according to an embodiment. Double-mask immobilization device 2400 couples with base headboard 108 and secures a patient's head during use of RTMM system 1000. According to embodiments, double-mask immobilization device 2400 provides for optimizing and creating a more accurate, reproducible and immobilized head and neck position during treatment or imaging, including a more accurate chin location Double-mask immobilization device 2400 comprises frame 2402 and two or more immobilization masks (such as, for example, upper mask 2404 and lower mask 2406). Frame 2402 comprises frame base 2410, one or more supports 2412, and frame mount 2414. According to embodiments, double-mask immobilization device 2400 couples to base headboard 108 of movement correction couch overlay 100. In one embodiment, the rigid or semi-rigid immobilization masks 2404-2406 hold a patient's face in a substantially immobile position relative to frame 2402 and/or base headboard 108, to which frame base 2410 may couple by one or more fasteners 404. In addition, or as an alternative, double-mask immobilization device 2400 may be utilized to secure a patient's head to other treatment or therapy devices or to prevent movement of a patient's head during a treatment, according to particular needs.

According to embodiments, each of immobilization masks 2404-2406 comprise an initially pliable material that may be formed to the shape of a patient's face and then hardened to hold the formed shape (by, for example, temperature, light, or other such hardening techniques). For example, immobilization masks 2404-2406 may comprise a thermoplastic material that becomes shapeable in a hot air oven or hot water bath. After becoming shapeable, the immobilization mask is formed to a patient who is placed on movement correction couch overlay 100 in a desired position. As immobilization masks 2404-2406 cool, they set and/or harden to maintain the shape of the face of the patient in the desired location.

As disclosed above, frame 2402 comprises frame base 2410, one or more supports 2412, and frame mount 2414. According to an embodiment, frame 2402 of double-mask immobilization device 2400 is an open frame that has a mask mounting surface at frame mount 2414 and is joined to a base mounting surface of frame base 2410 at the bottom by one or more supports 2412. In the illustrated embodiment, fame base 2410 is coupled to fame mount 2414 by supports 2412 comprising eight cylindrical members, two of the cylindrical members at each of the four corners of frame 2402. Although frame is shown and described as comprising eight cylindrical members joining fame mount 2414 with frame base 2410, embodiments contemplate any suitable number and configuration of supports or braces that allow for fitting of immobilization masks to the front and back of a patient's head, while providing support to double-mask immobilization device 2400 and the weight of the patient resting on the device.

The base mounting surface of frame base 2410 reversibly couples with a compatible board. The mask mounting surface surrounds the patient's head and serves as the anchor that holds the applied masks tight as they conform to the patient's head. According to embodiments, the base mounting surface for frame base 2410 and the mask mounting surface of frame mounts 2414 are sized and configured to fit a patient's head and a headrest and to allow a treatment provider to perform the fitting of the lower and upper immobilization masks to the patient.

Figure 25:
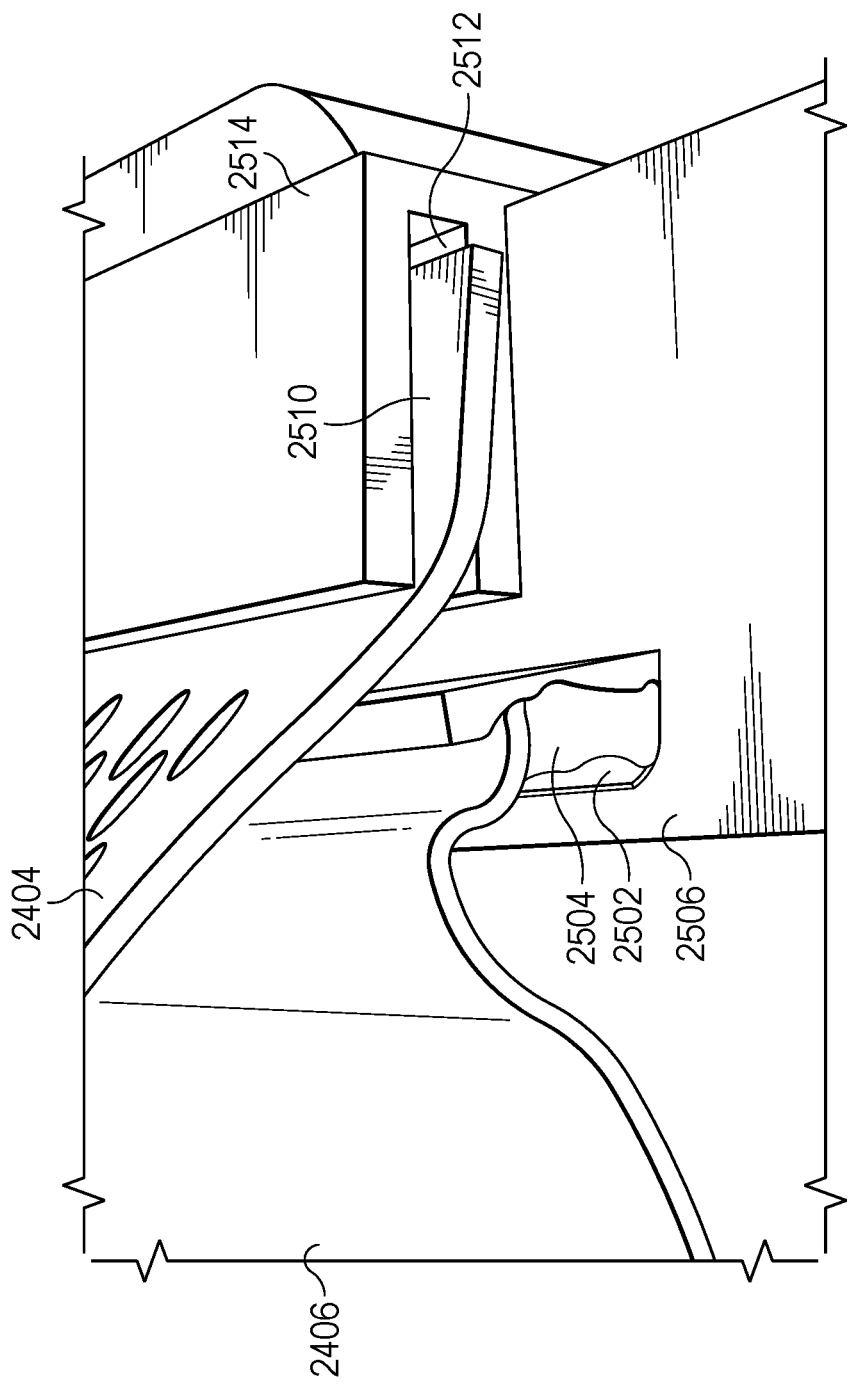
FIG. 25 illustrates mounting of the lower mask of the double-mask immobilization device, according to an embodiment.

FIG. 25 illustrates mounting of lower mask of double-mask immobilization device 2400, according to an embodiment. Lower mask 2406 couples with double-mask immobilization device 2400 by a set of channels 2502 which receive a set of lower mask tabs 2504 on the left and right sides of lower mask 2406. Channels 2502 may be placed within frame mount 2414 and/or mask mounting surface 2506.

Figure 26:
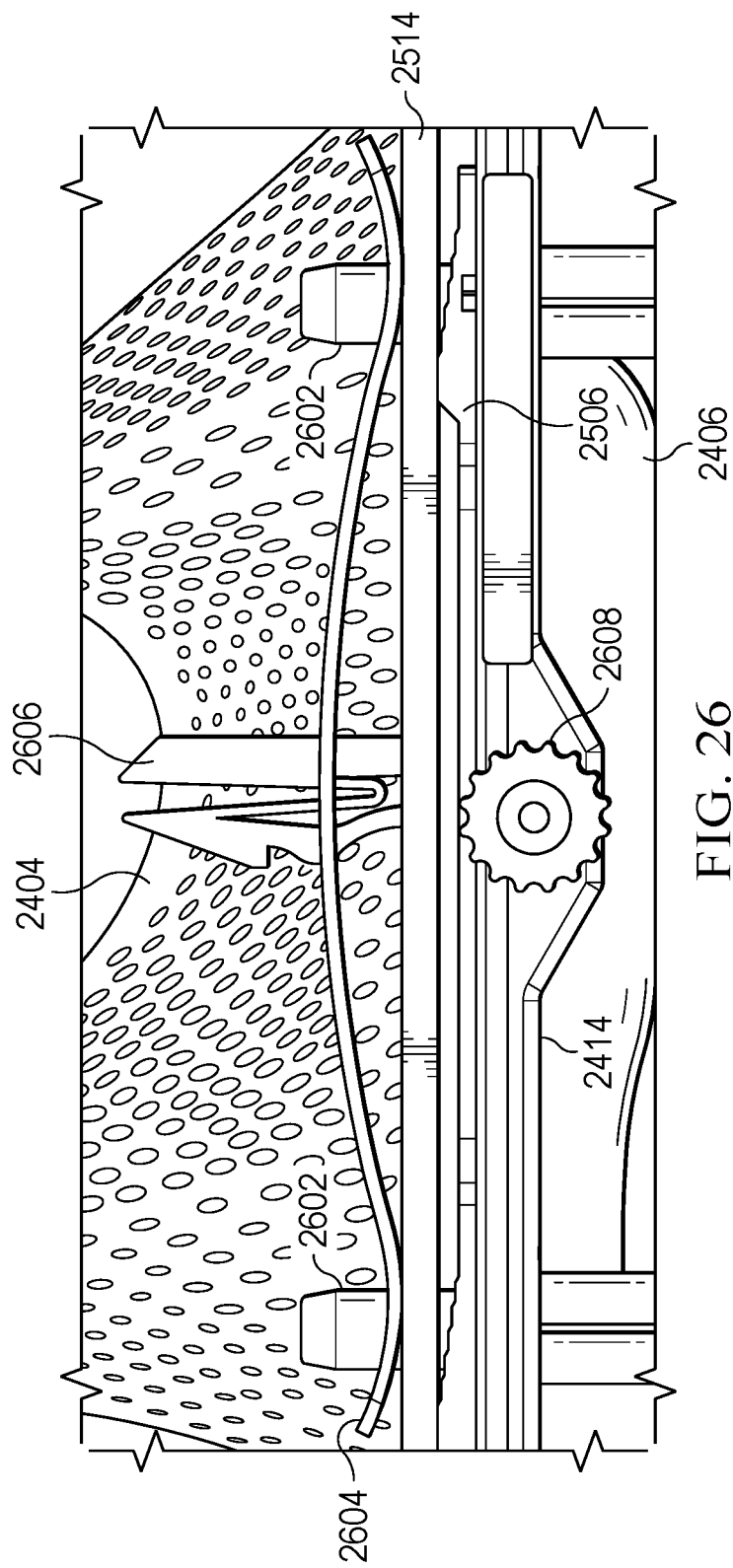
FIG. 26 illustrates mounting of the upper mask of the double-mask immobilization device, according to an embodiment.

FIG. 26 illustrates mounting of upper mask of double-mask immobilization device 2400, according to an embodiment. The upper mask mounting hardware may be attached to mask mounting surface 2506 of the frame or integrated into frame mount 2414. In one embodiment, the upper mask mounting hardware comprises four posts 2602 that mate with corresponding apertures in upper mask 2404. The upper mask mounting hardware may further comprise tension spring 2604 and latch 2606. Upper mask 2404 is locked down with constant pressure using a tension spring made of carbon fiber composite or other suitable spring material and is secured by engagement of spring 2604 with latch 2606. Upper mask 2404 is released from the tension by deforming latch 2606 (such as by pinching, squeezing, or the like) to allow latch 2606 to pass through the aperture of spring 2604 and slide spring 2604 from frame mount 2414.

In addition or as an alternative, upper mask 2404 may comprise upper mask tabs 2510 which are received by a corresponding slot 2512 in tab frame 2514 which secures upper mask 2404 within tab frame 2514. In an embodiment, tab frame 2514 and upper mask tabs 2510 comprise slots which secure over posts 2602 on either side of frame 2402. Knob 2608 is located on the side of frame 2402 and provides for raising and lowering the height of upper mask 2404 to better position the patient, providing a built-in alternative to using shims.

Figure 27:
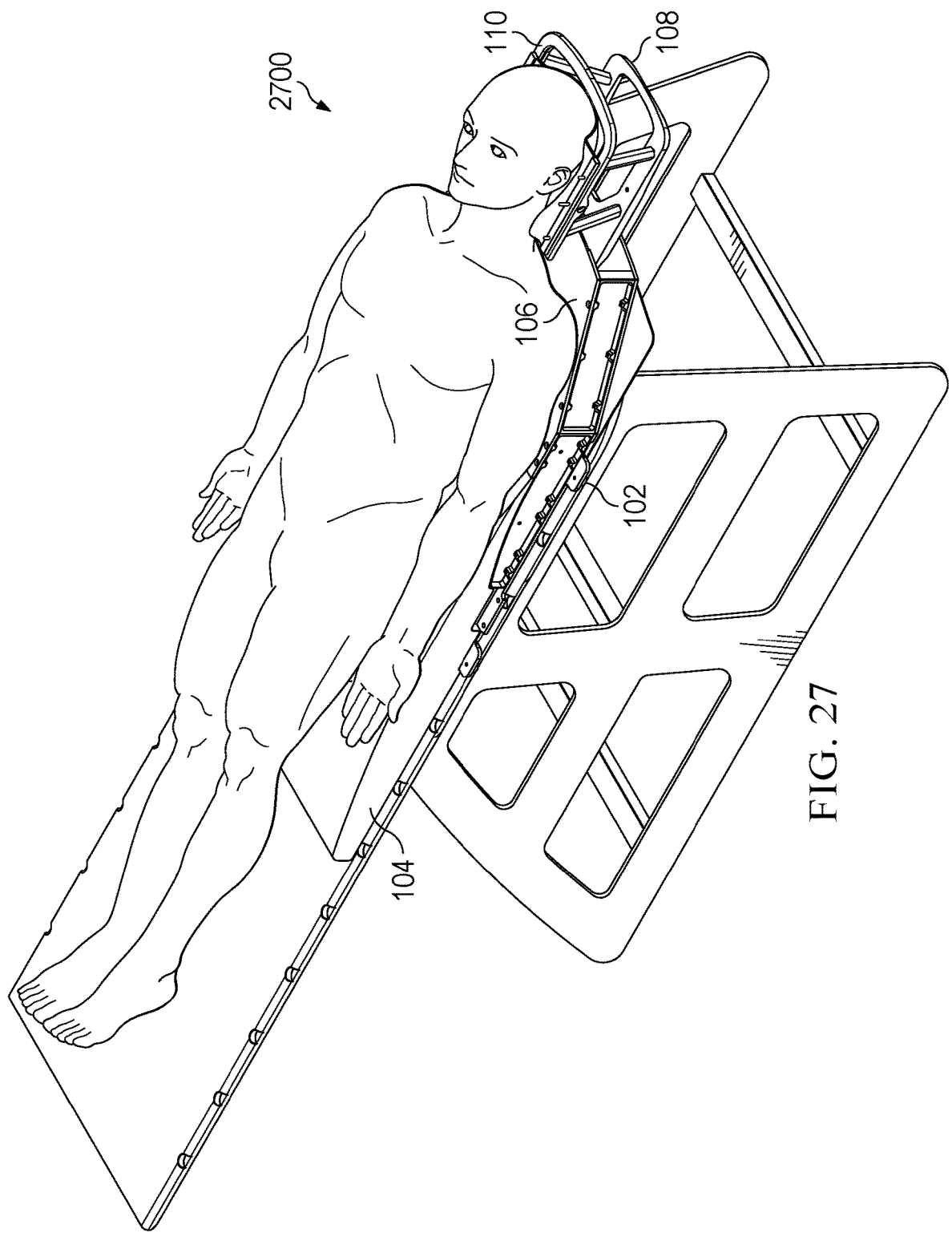
FIG. 27 illustrates an embodiment of the movement correction couch overlay comprising the surrogate system, according to an embodiment.

FIG. 27 illustrates an embodiment of movement correction couch overlay 100 comprising surrogate system 2700, according to an embodiment. Surrogate system 2700 is a flat indexable platform that can fit onto any couch and shares all features of movement correction couch overlay 100 frame, except for the lower enclosure housing for hexapod robot 112, which allows it to rest on top of the couch rather than requiring an overhang. Base headboard 108 of the surrogate system is coupled to a solid block inside the housing of the surrogate system, locking it into a position corresponding to the home position of robot 112 (i.e., an initial position robot 112 is set to after running through its initialization process). Surrogate system provides a stand-in for movement correction couch overlay 100 for testing and setup. Embodiments of base headboard 108 and headrest attachment 110 illustrated with surrogate system 2700 and any of the above embodiments may be used in combination with any other embodiment of movement correction couch overlay 100 disclosed herein, according to particular needs. In addition, the positioning of the patient on surrogate system 2700 is the same as that on the other embodiments of movement correction couch overlay 100 disclosed herein, including, for example, those showing phantom head model 430.

Although the coupling mechanisms described with respect to movement correction couch overlay 100 (and its various components), phantom head 430, double-mask immobilization device 2400, and other necessary and optional components of RTMM system 1000 have been described, embodiments contemplate any suitable coupling of components such as with adhesive, a weld joint, a solder joint, a fastener (e.g. a bolt and a nut, a screw, a clip, a rivet, a pin, hook and loop fastener, and/or the like), washers, retainers, straps, wrapping, wiring, and any combination of the foregoing. Additionally, although features of correction couch overlay 100 (and its various components), phantom head 430, double-mask immobilization device 2400, and other necessary and optional components of RTMM system 1000 are described as being separable, embodiments contemplate any feature being composed of more than one piece or multiple features being combined into a single piece, according to particular needs.

Although specific materials for each of the features of the present disclosure have been presented, embodiments contemplate various types of materials or combinations thereof that can readily be formed into shaped objects provided that the materials selected are consistent with the intended operation of correction couch overlay 100 (and its various components), phantom head 430, double-mask immobilization device 2400, and other necessary and optional components of RTMM system 1000. For example, the components may be formed of: rubbers (synthetic and/or natural); polymers, such as thermoplastics and thermosets; composites, such as carbon-fiber and KEVLAR®; metals; alloys; any other suitable material; and/or any combination of the foregoing.

According to embodiments, correction couch overlay 100 (and its various components), phantom head 430, double-mask immobilization device 2400, and other necessary and optional components of RTMM system 1000 comprise MR-safe materials, such that various materials used in the construction may be substituted for other optional materials. For example, according to an embodiment, fasteners (e.g., screws 404) used to fasten robot 112 to robot enclosure 114 may be made of metallic materials. When constructing an MR-Safe embodiment, fasteners (e.g., screws 404) may be made of non-metallic materials. Additionally, conductive materials (such as carbon fiber) may be substituted for non-conductive materials (such as Kevlar®).

Reference in the foregoing specification to "one embodiment", "an embodiment", or "another embodiment" means that a particular feature, structure, or characteristic described in connection with the embodiment is included in at least one embodiment of the invention. The appearances of the phrase "in one embodiment" in various places in the specification are not necessarily all referring to the same embodiment.

While the exemplary embodiments have been shown and described, it will be understood that various changes and modifications to the foregoing embodiments may become apparent to those skilled in the art without departing from the spirit and scope of the present invention.

What is claimed is:

1. A motion management system for providing accurate positioning of a patient comprising a control system and a horizontal support structure, the horizontal support structure further comprising a fixed surface and a movable surface actuated by a robotic device, the control system further configured to:
   receive target location information from one or more imaging devices or video output from a medical device providing treatment;
   generate a mapping of a patient location or a patient movement by scanning a visual field that includes the patient and the horizontal support structure;
   interpret the mapping to calculate a new position based on a detected deviation of a patient position or a patient movement from a target position;
   send instructions to the robotic device to actuate the movable surface to the new position; and
   receive position status information from the robotic device.

2. The system of claim 1, wherein the detected deviation is further determined by an internal anatomy of the patient as obtained from medical imaging or surface tracking of external anatomical features of the patient.

3. The system of claim 1, wherein the detected deviation is further determined by calculating a target position relative to reflective points placed on the patient, analyzing and tracking a surface geometry of a physical patient feature or using continuous x-ray scans of the patient during treatment.

4. The system of claim 1, wherein the robotic device is configured to actuate the movable surface in six degrees of freedom with respect to the fixed surface.

5. The system of claim 1, wherein the robotic device actuates the movable service via mechanical, pneumatic or hydraulic actuators.

6. The system of claim 1, wherein the target location information is determined by video capture and analysis from the medical device.

7. The system of claim 1, wherein the control system is configured to receive manual position instructions.

8. A computer-implemented method for motion management to provide accurate positioning for a patient, comprising:
   receiving, by a control system comprising a computer, target location information from one or more imaging devices or video output from a medical device providing treatment;
   generating, by the computer, a mapping of a patient location or a patient movement by scanning a visual field that includes the patient and a horizontal support structure;
   interpreting, by the computer, the mapping to calculate a new position based on a detected deviation of the patient position or patient movement from a target position;
   sending, by the computer, instructions to a robotic device to actuate a movable surface to the new position; and
   receiving, by the computer, position status information from the robotic device.

9. The computer-implemented method of claim 8, wherein the detected deviation is further determined by an internal anatomy of the patient as obtained from medical imaging or surface tracking of external anatomical features of the patient.

10. The computer-implemented method of claim 8, wherein the detected deviation is further determined by calculating a target position relative to reflective points placed on the patient, analyzing and tracking a surface geometry of a physical patient feature or using continuous x-ray scans of the patient during treatment.

11. The computer-implemented method of claim 8, wherein the robotic device is configured to actuate the movable surface in six degrees of freedom with respect to the fixed surface.

12. The computer-implemented method of claim 8, wherein the robotic device actuates the movable service via mechanical, pneumatic or hydraulic actuators.

13. The computer-implemented method of claim 8, wherein the target location information is determined by video capture and analysis from the medical device.

14. The computer-implemented method of claim 8, wherein the control system is configured to receive manual position instructions.

15. A non-transitory computer-readable storage medium embodied with software for motion management to provide accurate positioning for a patient, the software when executed:

receives, by a control system comprising a computer, target location information from one or more imaging devices or video output from a medical device providing treatment;

generates a mapping of a patient location or a patient movement by scanning a visual field that includes the patient and a horizontal support structure, interprets the mapping to calculate a new position based on a detected deviation of the patient position or patient movement from a target position;

sends instructions to a robotic device to actuate a movable surface to the new position; and receives position status information from the robotic device.

16. The non-transitory computer-readable storage medium of claim 15, wherein the software when executed determines the deviation by an internal anatomy of the patient as obtained from medical imaging or surface tracking of external anatomical features of the patient.

17. The non-transitory computer-readable storage medium of claim 16, wherein the software when executed determines the deviation by calculating a target position relative to reflective points placed on the patient, analyzing and tracking a surface geometry of a physical patient feature or using continuous x-ray scans of the patient during treatment.

18. The non-transitory computer-readable storage medium of claim 15, wherein the robotic device is configured to actuate the movable surface in six degrees of freedom with respect to the fixed surface.

19. The non-transitory computer-readable storage medium of claim 15, wherein the robotic device actuates the movable service via mechanical, pneumatic or hydraulic actuators.

20. The non-transitory computer-readable storage medium of claim 15, wherein the control system is configured to receive manual position instructions.

* * * * *